US010184115B2

(12) United States Patent
Ludwig et al.

(10) Patent No.: US 10,184,115 B2
(45) Date of Patent: Jan. 22, 2019

(54) MUTATED CELLOBIOSE DEHYDROGENASE WITH INCREASED SUBSTRATE SPECIFICITY

(71) Applicant: DIRECTSENS GMBH, Klosterneuburg (AT)

(72) Inventors: Roland Ludwig, Vienna (AT); Christoph Sygmund, Klosterneuburg (AT); Wolfgang Harreither, Vienna (AT); Roman Kittl, Vienna (AT); Alfons Felice, Vienna (AT)

(73) Assignee: DIRECTSENS GMBH, Klosterneuberg (AT)

( * ) Notice: Subject to any disclaimer, the term of this patent is extended or adjusted under 35 U.S.C. 154(b) by 0 days.

(21) Appl. No.: 14/383,848

(22) PCT Filed: Mar. 6, 2013

(86) PCT No.: PCT/EP2013/054476
§ 371 (c)(1),
(2) Date: Sep. 8, 2014

(87) PCT Pub. No.: WO2013/131942
PCT Pub. Date: Sep. 12, 2013

(65) Prior Publication Data
US 2015/0083611 A1    Mar. 26, 2015

(30) Foreign Application Priority Data
Mar. 8, 2012 (EP) ..................................... 12158605

(51) Int. Cl.
| *C12N 9/04* | (2006.01) |
| *C12N 9/96* | (2006.01) |
| *C12Q 1/00* | (2006.01) |
| *G01N 33/66* | (2006.01) |
| *G01N 33/68* | (2006.01) |
| *G01N 27/327* | (2006.01) |

(52) U.S. Cl.
CPC ............ *C12N 9/0006* (2013.01); *C12N 9/96* (2013.01); *C12Q 1/006* (2013.01); *C12Y 101/99018* (2013.01); *G01N 27/3271* (2013.01); *G01N 33/66* (2013.01); *G01N 33/689* (2013.01); *G01N 2333/902* (2013.01); *G01N 2400/00* (2013.01)

(58) Field of Classification Search
None
See application file for complete search history.

(56) References Cited

U.S. PATENT DOCUMENTS

2009/0181874 A1*  7/2009  Souter .................. A61K 8/66
510/300

2011/0045513 A1*  2/2011  Takenaka ............... C07K 14/80
435/14
2011/0306076 A1*  12/2011  Ludwig ................ C12N 9/0006
435/26

FOREIGN PATENT DOCUMENTS

WO    WO 2010/097462      9/2010
WO    WO-2010-0126139   * 11/2010

OTHER PUBLICATIONS

Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Guo et al. Protein tolerance to random amino acid change, Proc Natl Acad Sci U S A. Jun. 22, 2004;101(25):9205-10. Epub Jun. 14, 2004.*
B. Martin Hallberg, et al., "Crystal Structure of the Flavoprotein Domain of the Extracellular Flavocytochrome Cellobiose Dehydrogenase," J. Mol. Biol. (2002) 315, 421±434.
C. Sygmund, et al. "A new generation of glucose biosensors—engineering cellobiose dehydrogenase for increased direct electron transfer," New Biotechnology, vol. 25S. Sep. 2009.
Federico Tasca, et al., "A third generation glucose biosensor based on cellobiose dehydrogenase from Corynascus thermophilus and single-walled carbon nanotubes," Analyst, 136, 2033, (2011).
Federico Tasca, et al., "Cellobiose Dehydrogenase Aryl Diazonium Modified Single Walled Carbon Nanotubes: Enhanced Direct Electron Transfer through a Positively Charged Surface," Analytical Chemistry, 83, pp. 3042-3049. 2001.
Federico Tasca, et al., "Increasing the Coulombic Efficiency of Glucose Biofuel Cell Anodes by Combination of Redox Enzymes," Biosensors and Bioelectronics 25 (2010).
Fei Mao, et al., "Long Tethers Binding Redox Centers to Polymer Backbones Enhance Electron Transport in Enzyme "Wiring" Hydrogels," J. Am. Chem. Soc. 2003, 125, 4951-4957.
Fusheng Li and James I. Mullins, "Site-Directed Mutagenesis Facilitated by DpnI Selection on Hemimethylated DNA," Methods in molecular biology. Feb. 2002; 182:19-27.
Gulnara Safina, et al., "A simple and sensitive method for lactose detection based on direct electron transfer between immobilised cellobiose dehydrogenase and screen-printed carbon electrodes," Electrochimica Acta 55 (2010) 7690-7695.
Gunnar Henriksson, et al., "Substrate specificity of cellobiose dehydrogenase from Phanerochaete chrysosporium," Biochimica et Biophysica Acta 1383 1998. 48-54.
Marcel Zamocky, et al. "Cloning, sequence analysis and heterologous expression in Pichia pastoris of a gene encoding a thermostable cellobiose dehydrogenase from Myriococcum thermophilum," Protein Expression and Purification 59 (2008) 258-265.

(Continued)

*Primary Examiner* — Iqbal H Chowdhury
(74) *Attorney, Agent, or Firm* — Norton Rose Fulbright US LLP

(57) ABSTRACT

The present invention relates to a modified cellobiose dehydrogenase (CDH) or its functional flavodehydrogenase domain having glucose oxidation activity and a reduced maltose oxidation activity as compared to the unmodified CDH or its functional flavodehydrogenase domain, nucleic acids encoding said enzyme or domain, electrodes with said enzyme or domain and methods of producing and using the same.

13 Claims, 5 Drawing Sheets

Figure 2:
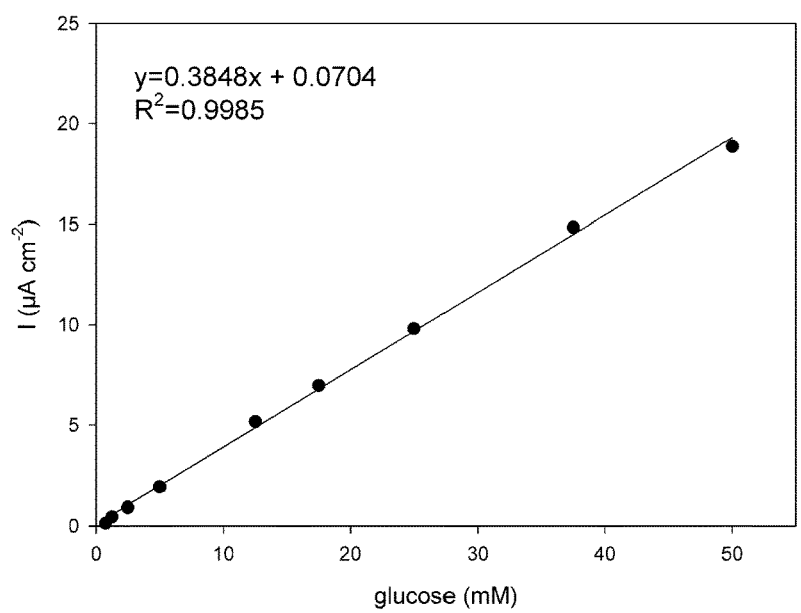

Specification includes a Sequence Listing.

(56) References Cited

OTHER PUBLICATIONS

Marcel Zamocky, et al., "Cellobiose Dehydrogenase—A Flavocytochrome from Wood-Degrading, Phytopathogenic and Saprotropic Fungi," Current Protein and Peptide Science, 7, pp. 255-280 (2006).
Roland Ludwig, et al., "Cellobiose Dehydrogenase: A Versatile Catalyst for Electrochemical Applications," ChemPhysChem 2010, 11, 2674-2697.
Sandra Abad, et al., "Stepwise engineering of a Pichia pastoris D-amino acid oxidase whole cell catalyst," Microbial Cell Factories 2010, 9:24.
Wolfgang Harreither, et al, "Investigation of Graphite Electrodes Modified with Cellobiose Dehydrogenase from the Ascomycete Myriococcum thermophilum," Electroanalysis 19, 2007, No. 2-3, 172-180.
Wolfgang Harreither, et al., "Catalytic Properties and Classification of Cellobiose Dehydrogenases from Ascomycetes," Applied and Environmental Microbiology, Mar. 2011, p. 1804-1815.

* cited by examiner

Fig.1

C.attro: SEQ ID NO: 5; H.haema: SEQ ID NO: 3; C.therm: SEQ ID NO: 7;
N.crass: SEQ ID NO: 11; M.therm: SEQ ID NO: 1; S.bisby: SEQ ID NO: 9;

```
                      20                  40         **+**+****
C.attro : FDYIVVGGGAGGIPTADKLSEAGKSVLLIEKGIASTAEHGGTLGPEWLEGNDLTRFDVPGLCNQIWVDSK  :  70
H.haema : YDYIVVGAGAGGIPLADKLSEAGKSVLLIEKGPPSSGRWGGTLKPEWLKDTNLTRFDVPGLCNEIWVNSA  :  70
C.therm : YDYIVVGAGAGGITVADKLSEAGHKVLLIEKGPPSTGLWNGTMKPEWLEGTDLTRFDVPGLCNQIWVDSA  :  70
N.crass : FDYIVVGGGAGGIPVADKLSESGKSVLLIEKGFASTGEHGGTLKPEWLNNTSLTRFDVPGLCNQIWKDSD  :  70
M.therm : FDYIVVGCGAGGIPAADKLSEACKSVLLIEKGFASTANTCCTLGPEWLECHDLTRFDVPGLCNQIWVDSK  :  70
S.bisby : YDYIVVGSGAGGIPIADKLTEAGKKVLLIEKGPPSSGRYDGKLKPTWLEGTNLTRFDVPGLCNQIWVDSA  :  70

80         ******100                120                140
C.attro : GIACEDTDQMAGCVLGGGTAVNAGLWFKPYSLDWDYLFPSGWKYRDIQAAIGRVFSRIPGTDAPSTDGKR  : 140
H.haema : GVACTDTDQMAGCVLGGGTAVNAGLWWKPYNLDWDYNFPRGWKSRDMAAATRRVFSRIPGTDNPSMDGKR  : 140
C.therm : GIACTDTDQMAGCVLGGGTAVNAGLWWKPHPADWDDNFPHGWKSSDLADATERVFSRIPGTWHPSQDGKL  : 140
N.crass : GIACSDTDQMAGCVLGGGTAINAGLWYKPYTKDWDYLFPSGWKGSDIAGATSRALSRIPGTTTPSQDGKR  : 140
M.therm : GIACEDTDQMAGCVLGGGTAVNAGLWFKPYSLDWDYLFPDGWKYNDVQPAINRALSRIPGTDAPSTDGKR  : 140
S.bisby : GIACRDTDQMAGCVLGGGTAVNAGLWWKPNPIDWDYNFPSGWKSSEMIGATNRVFSRIGGTTVPSQDGKT  : 140

160                180                200
C.attro : YYQQGFDVLAGGLSAGGWNKVTANSSPDKKNRTFSNAPFMFSGGERGGPLATYLTSAKKRSNFNLWLNTS  : 210
H.haema : YLQQGFEILAGGLKAAGWTEVTANDAPNKKNHTYSHSPFMFSGGERGGPMGTYLVSASRRKNFHLWTGTA  : 210
C.therm : YRQEGFEVISQGLANAGWREVDANQEPSEKNRTYSHSVFMFSGGERGGPLATYLASAAQRSNFNLWVNTS  : 210
N.crass : YLQQGFEVLANGLKASGWKEVDSLKDSEQKNRTFSHTSYMYINGERGGPLATYLVSAKKRSNFKLWLNTA  : 210
M.therm : YYQEGFEVLSKGLAAGGWTSVTANNAPDKKNRTFAHAPFMFAGGERNGPLGTYFQTAKKRNNFDVWLNTS  : 210
S.bisby : YYQQGFNVLSSGLKAAGWTSVSLNNAPAQKNRTYGAGPFMFSGGERGGPLATYLATAKKRGNFDLWTNTQ  : 210

220                240                260                280
C.attro : VKRVIREGGHVTGVEVEPFRTGGYQGIVNVTAVSGRVVLSAGTFGSAKILLRGGIGPADQLEVVKASKID  : 280
H.haema : VKRVVRTGGHITGLEVEPFVNGGYTGVVNVTSITGRVVLSAGAFGSAKILLRSGIGPEDQLEIVKSS-TD  : 279
C.therm : VRRAIRTGPRVSGVELECLADGGFNGTVNLK-EGGGVIFSAGAFGSAKLLLRSGIGPEDQLEIVASS-KD  : 278
N.crass : VKRVIREGGHITGVEVEAFRNGGYSGIIPVTNTTGRVVLSAGTFGSAKILLRSGIGPKDQLEVVKAS-AD  : 279
M.therm : VKRVIREGGHITGVEVEPFRDGGYEGIVPVTKVTGRVILSAGTFGSAKILLRSGIGPEDQLEVVAASEKD  : 280
S.bisby : VKRVIRQGGHVTGVEVENYNGDGYKGTVKVTPVSGRVVLSAGTFGSAKLLLRSGIGPKDQLAIVKNS-TD  : 279

300                320                340
C.attro : GPTMISNASWIPLPVGYNLDDHLNTDTVITHPDVAFYDFYEAWNTPIEADKNSYLSSRTGILAQAAPNIG  : 350
H.haema : GPTMISDSSWITLPVGYNLEDHTNTDTVVTHPDVVFYDFYEAG-HPNVTDKDLYLNSRAGILAQAAPNIG  : 348
C.therm : GETFISKNDWIKLPVGHNLIDHLNTDLIITHPDVVFDFYAAWDNPITEDKEAYLNSRSGILAQAAPNIG  : 348
N.crass : GPTMVSNSSWIDLPVGHNLVDHTNTDTVIQHNNVTFYDFYKAWDNPNTTDMNLYLNGRSGIFAQAAPNIG  : 349
M.therm : GPTMIGNSSWINLPVGYNLDDHLNTDTVISHPDVVFYDFYEAWDDPIESDKNSYLESRTGILAQAAPNIG  : 350
S.bisby : GPTMASERDWINLPVGYNLEDHTNTDIVISHPDVVHYDFYEAWTAPIESDKTAYLGKRSGILAQAAPNIG  : 349

360        ****+**   380               400              420
C.attro : PMMWEEIKGADGIVRQLQWTARVEGSFDTPNG-QAMTISQYLGRGATSRGRMTITPSLTTVVSDVPYLKD  : 419
H.haema : PMFWEEIKGKDGVVRQLQWTARVEGSAGTPNG-YAMTMSQYLGRGAKSRGRMTITKALTTVVSTVPYLQD  : 417
C.therm : PLMWEEVTPSDGITRQFQWTCRVEGDSSKTNSTHAMTLSQYLGRGVVSRGRMGITSGLTTTVAEHPYLHN  : 418
N.crass : PLFWEEITGADGIVRQLHWTARVEGSFETPDG-YAMTMSQYLGRGATSRGRMTLSPTLNTVVSDLPYLKD  : 418
M.therm : PMFWEEIVGADGIVRQLQWTARVEGSLGAPNG-HTMTMSQYLGRGATSRGRMTITPSLTTIVSDVPYLKD  : 419
S.bisby : PLFFDEVRGADNIVRSIQYTARVEGNSVVPNG-KAMVISQYLGRGAVSRGRMTISQGLNTIVSTAPYLSN  : 418

440         *      460          ***+*** 480
C.attro : PNDKEAVIQGIVNLQNALK-NVAGLTWTYPNSSITPREYVDNMVVSPSNRRANHWMGTAKIGTDDGRLAG  : 488
H.haema : KNDVEAVIQGIKNLQAALS-NVKNLTWTYPPSNTTVEDFVNNMLVSYTNRRSNHWIGTNKLGTDDGRSRG  : 486
C.therm : DGDLEAVIQGIQNVVDALS-QVPDLEWVLPPPNTTVEEYVNSLIVSPANRRANHWMGTAKMGLDDGR-SG  : 486
N.crass : PNDKAAVVQGIVNLQKALA-NVKGLTWAYPSANQTAADFVDKQPVTYQSRRSNHWMGTNKMGTDDGR-SG  : 486
M.therm : PNDKEAVIQGIINLQNALQ-NVANLTWLFPNSTITPREYVESMVVSPSNRRSNHWMGTNKLGTDDGR-KG  : 487
S.bisby : VNDLEAVIKSLENIANSLTSKVKNLKIEWPASGTSIRDHVTNMPLDPATRRANHWIGTNKIGTKDGRLTG  : 488

500                520                540                560
C.attro : GSAVVDLNTKVYGTDNLFVVDASIFPGTPTTNPSAYIVTAAEHASQRILGLAAPKPVGKWGQCGGRQWTG  : 558
H.haema : GSAVVDLNTKVYGTDNLFVVDAGIFPGHITTNPTSYIVIAAERASERILDLPPARAQPRFAQCGGRTWTG  : 556
C.therm : GSAVVDLNTKVYGTDNLFVVDASIFPGMSTGNPSAMIVIVAEQAAQRILSLRY----------------  : 539
N.crass : GTAVVDTNTRVYGTDNLYVVDASIFPGVPTTNPTAYIVVAAEHAAAKILAQPANEAVPKWGWCGGPTYTG  : 556
M.therm : GSAVVDLDTRVYGTDNLFVIDASIFPGVPTTNPTSYIVVAAEHASSRILALPDLEPVPKYGQCGGREWTG  : 557
S.bisby : GDSVVDLNTKVYGTDNLFVVDASIFPGMVTTNPSAYIVIAAEHAASKILSLPTAKAAAKYEQCGGLEYNG  : 558
```

```
                     580
C.attro : SFQCVSGTKCEVVNEWYSQCL : 579
H.haema : SFQCAAPYTCQYRNERYSQCR : 577
C.therm : -------------------- : -
N.crass : SQTCQAPYKCEKQNDWYWQCV : 577
M.therm : SFVCADGSTCEYQNEWYSQCL : 578
S.bisby : NFQCASGLTCTWLNDYYWQCT : 579
```

Continuation of Fig. 1

C312Y

C312Y/W316R

MUTATED CELLOBIOSE DEHYDROGENASE WITH INCREASED SUBSTRATE SPECIFICITY

This application is a national phase application under 35 U.S.C. § 371 of International Application No. PCT/EP2013/054476 filed 6 Mar. 2013, which claims priority to European Patent Application No. 12158605.1 filed 8 Mar. 2012. The entire contents of each of the above-referenced disclosures is specifically incorporated herein by reference without disclaimer.

The field of the present invention relates to recombinant enzyme modification to modify substrate specificity.

Cellobiose dehydrogenase (EC 1.1.99.18, CDH) was first discovered in 1974 in the extracellular enzyme system of *Phanerochaete chrysosporium* and later on in several other basidiomycetous fungi. Cloning and sequence analysis of CDHs are e.g. described in Zamocky et al., 2008. A special characteristic of this enzyme is its composition: the combination of a catalytically active flavodehydrogenase domain (also called "flavin domain"), hosting a non-covalently bound FAD, and a haem domain, with a haem b as a cofactor. Both domains are connected by a linker. By its catalytic activity the natural substrate cellobiose is oxidised in a reaction which reduces the FAD of the flavin domain.

CDH or its flavodehydrogenase domain oxidises carbohydrates like its natural substrates cellobiose and cellooligosaccharides and others like lactose and maltose. CDHs have been discovered and modified previously to be capable of converting glucose efficiently (Harreither et al., 2011; WO 2010/097462 A; Sygmund et al., 2009).

It was shown recently that maltose present in blood can negatively affect the accuracy of the glucose determination by glucose dehydrogenase (having a pyrrolinoquinolone quinone cofactor) based glucose meters (in the web at www.fda.gov/BiologicsBloodVaccines/SafetyAvailability/ucm155099.htm). Increased maltose levels can occur after treatments with immune globulin products containing maltose, peritoneal dialysis solutions containing isodextrin (which is metabolised to maltose and other oligosaccharides) or maltose containing infusion solutions. To circumvent that problem, FAD-dependent glucose dehydrogenase was mutated to exhibit a higher substrate specificity for glucose (EP 1 739 174 A). CDHs tested for maltose conversion so far showed activity with this substrate (Zamocky et al., 2006).

It is a goal of the present invention to provide a cellobiose dehydrogenase or its catalytically active flavodehydrogenase domain, which is capable to selectively detect glucose in the presence of maltose, especially with direct electron transfer based electrodes or mediated electron transfer-based electrodes to provide suitable analytically useful sensors.

The present invention relates to recombinant modified cellobiose dehydrogenases (CDH) with reduced maltose turnover, alone, or in combination with an increased glucose turnover. The aim is to reduce the effect of any maltose concentration present in a sample matrix on glucose detection. Preferred modified cellobiose dehydrogenase enzymes of the invention are optimized for use in biosensors based on direct electron transfer ($3^{rd}$ generation) or based on mediated electron transfer ($2^{nd}$ generation).

To increase the performance of CDH as selective electrode catalyst for glucose, the reduction of maltose oxidation activity alone or in combination with an increase of glucose oxidation activity was pursued by genetic modification. With the general description of modifying a CDHs flavodehydrogenase domain, a domain of high homology in all CDHs, it is possible to modify any CDH according to the principles outlined herein in order to decrease maltose sensitivity. Thus the present invention provides a modified cellobiose dehydrogenase (CDH) or its functional flavodehydrogenase domain having glucose oxidation activity and a reduced maltose oxidation activity as compared to the unmodified CDH or its functional flavodehydrogenase domain. The invention further provides a method of oxidizing glucose with the CDH of the invention. Such a method is preferably used in the analytical detection of glucose in a sample.

Most CDHs are capable of oxidizing glucose. The oxidation reaction can be detected e.g. by monitoring electron acceptors for the redox reaction such quinones, like as DCIP (2,6-dichloroindophenol) o- or p-benzoquinone or derivatives thereof, methylene blue, methylene green, Meldola's blue, potassium ferricyanide, ferricenium hexafluorophosphate, $FeCl_3$ or cytochrome c (the latter being a haem domain cofactor) or simply by determining electric current or voltages on an electrode, the electron acceptor being the electrode surface.

WO 2010/097462 A describes isolated CDHs and modifications of CDHs to increase glucose oxidation at a pH of 7.4. WO 2010/097462 A especially focuses on increasing the pH optimum and interaction between the flavin domain and the haem domain. Such CDHs are preferred starting CDHs for the present invention, but the invention is not limited to glucose oxidation activity at pH 7.4. Any pH is suitable for the present invention. Preferably the CDH of the invention has glucose oxidation activity at a pH of between 2 and 9, preferably between 3 and 8.5, especially preferred between 4 and 8, even more preferred between 5 and 7.5 or between 5.5 and 7. Furthermore it is not necessary to use an entire CDH; the flavin domain, even without the haem domain, is sufficient for catalytical activity. The domain is therefore referred to as "functional domain" as it has the function of oxidizing glucose with a suitable electron acceptor. The activity is excerted by either the whole enzyme cellobiose dehydrogenase or the catalytically active flavodehydrogenase domain.

Wild type CDHs have an undesirable activity to oxidize maltose. This modification according to the present invention should now be understood in that the inventive CDHs deviate from the wild-type CDHs by this substantially decreased maltose oxidation activity. This substantially decreased maltose oxidation activity may be in combination with an increased glucose oxidation activity.

Preferred modified CDHs or their functional flavodehydrogenase domain are of a CDH of *Myriococcum thermophilum, Corynascus thermophilus, Chaetomium atrobrunneum, Hypoxylon haematostroma, Neurospora crassa* or *Stachybotrys bisby*. Such unmodified CDHs are described in WO 2010/097462 A and in sequences of SEQ ID NO: 1, 3, 5, 7, 9 and 11 herein. "Unmodified" as used herein is a CDH without the inventive modification that decreases maltose oxidation activity or maltose sensitivity. There may be modifications that increase interaction between the favin and the haem domains if an entire CDH is used (such as described in WO 2010/097462).

The modified CDH or its functional flavodehydrogenase domain preferably comprises a modified flavodehydrogenase domain based on one of the unmodified flavodehydrogenase domains according to amino acids 251-828 of SEQ ID NO: 1, amino acids 263-839 of SEQ ID NO: 3, amino acids 253-831 of SEQ ID NO: 5, amino acids 249-787 of SEQ ID NO: 7, amino acids 251-829 of SEQ ID NO: 9, or amino acids 253-829 of SEQ ID NO: 11. Preferably the inventive modified flavodehydrogenase domain has a sequence with at least 50%, preferably at least 55%, at least 60%, at least 65%, at least 70%, at least 75%, at least 80%, at least 85%, at least 90%, at least 95%, at least 98%, in particular preferred at least 99%, sequence identity with one of said unmodified flavodehydrogenase domains and further comprises at least one amino acid modification reducing the maltose oxidation activity. Such an amino acid modification or mutation may be an amino acid substitution, deletion or addition. Homologous CDHs or flavodehydrogenase domains within these sequence requirements can be readily identified by sequence comparisons such as by sequence alignment using publicly available tools, such as BLASTP, ClustalW or FastDB. Preferably, a homologous or modified CDH or the domain thereof has 1, 2, 3, 4, 5, 6, 7, 8, 9, 10, at least 11, at last 13, at least 15, at least 17, at least 20, at least 25, at least 30, at least 40, at least 50, at least 60, at least 80, at least 100 and/or up to 100, up to 80, up to 60, up to 50, up to 40, up to 30, up to 30, up to 20, up to 15 amino acid substitutions, deletions, insertions or modifications, and any ranges between these values, as compared to any one of the CDHs of SEQ ID NOs 1, 3, 5, 7, 9 or 11 or any of their flavodehydrogenase domains.

Preferably the inventive CDH has at least 1, 2, 3, 4, 5, 6, 7, 8, 9 or 10 or more amino acid modifications to reduce maltose oxidation activity as can be determined by the assays described herein, such as by using DCIP as electron acceptor or on an electrode. Such amino acid modifications are usually in the catalytically active center of the flavin domain.

The inventive amino acid modifications are of amino acids responsible for the maltose binding and/or catalysis, especially modifications in the catalytic site involved in substrate interaction. A prediction of such modifications can be made by computational methods using e.g. molecular docking into crystal structures such as of PDB database entry "1 kdg".

The effect of modified amino acids in the active site and the substrate binding site can be determined for homogeneous catalysis by photometric methods and for heterogeneous catalysis by electrochemical measurements using enzyme electrodes as described herein.

The methods for the modification may be any known in the art such as amino acid mutations, including amino acid substitutions, deletions or additions but also chemical modification/derivatisation of amino acid side chains.

The inventive enzyme or domain is usually recombinantly expressed. Also provided are preparations comprising the modified CDH or domain. The term "enzyme" or "enzyme preparation" as used herein refers to a cellobiose dehydrogenase or its flavodehydrogenase domain from a specified organism which is at least about 20% pure, preferably at least about 40% pure, even more preferably at least about 60% pure, even more preferably at least 80% pure and most preferably at least 90% pure, as determined by polyacrylamide gel electrophoresis (SDS-PAGE).

The present invention relates to modified/genetically engineered cellobiose dehydrogenases from existing protein scaffolds, which oxidise maltose less efficiently with or without a more efficient glucose turnover than the currently known cellobiose dehydrogenases. The kinetic constants of the enzymes responsible for this effect are preferably a higher $K_M$ value and lower $k_{cat}$ value for maltose alone or in combination with a lower $K_M$ value and higher $k_{cat}$ value for glucose than the currently characterised enzymes.

Preferably the $K_M$ value of the cellobiose dehydrogenase or its functional flavodehydrogenase domain for a maltose oxidation reaction is above 50 mM, preferably as determined with the CDH or said domain being immobilized on an electrode. Of course, the modified CDH or the flavin domain has still activity for an electrocatalytic oxidation of glucose. Especially preferred the CDH or flavin domain has the property that a signal of maltose during glucose detection or glucose concentration determination is below 5%; particularly the signal, e.g. electrode current or electrochemical reduction of an electron acceptor, of 30 mM maltose in a solution comprising mM glucose solution is below 5%. In preferred embodiments of the invention the maltose oxidation activity of the CDH is reduced in relation to glucose oxidation activity. Especially preferred the concentration dependency of the maltose oxidation is reduced so that—if maltose is present—only a substantially constant contribution of maltose to the signal is detected in relation to a glucose signal.

It is understood that one of skill in the art may engineer the mentioned or other cellobiose dehydrogenases to obtain the modified CDH or the active flavodehydrogenase domain using the principles outlined herein like the rational enzyme engineering via site-directed mutagenesis or directed evolution approaches (e.g., gene shuffling, error-prone PCR, etc.) and subsequent screening of the generated diversity. The techniques to introduce a mutation into the nucleic acid sequence to exchange one nucleotide for another nucleotide with the aim to exchange one amino acid for another in the resulting protein may be accomplished by site-directed mutagenesis using any of the methods known in the art.

Preferred modifications (amino acid deletions, substitutions or additions) of the CDH of the flavodehyrogenase domain in order to decrease the activity of maltose oxidation, optionally together with an increase of glucose activity are preferably situated in the active site of CDH, which can be divided into the catalytic site (C-site) and substrate binding site (B-site) of the flavodehydrogenase domain (Hallberg et al., 2002). The active site is formed by the amino acids Phe 251 to Phe 283, Ala 284 to Leu 352 and Asp 611 to Ser 772 of the *M. thermophilum* CDH of SEQ ID NO: 1.

In especially preferred embodiments the modification of the modified CDH or its functional flavodehydrogenase domain is a modification of at least one amino acid corresponding to any one of amino acids 310-320, 342-347, 618-624 or 718-725, and most preferably of any one of amino acids 312, 313, 316, 622 and 721, of the *M. thermophilum* cellobiose dehydrogenase of SEQ ID NO: 1, or any combination thereof. The amino acids are closely located to maltose binding to the flavin domain or catalytic oxidation of maltose. Preferred amino acids for modification are thus amino acids corresponding to amino acids 310, 311, 312, 313, 314, 315, 316, 317, 318, 319, 320, 342, 343, 344, 345, 346, 347, 599, 600, 601, 602, 603, 604, 605, 606, 607, 608, 609, 610, 610, 611, 612, 613, 614, 615, 616, 617, 618, 619, 620, 621, 622, 623, 624, 625, 718, 719, 720, 721, 722, 723, 724, 725 or any combination thereof of the CDH of SEQ ID NO: 1.

Especially preferred amino acid residues involved in substrate binding in the B-site and suitable for modification are corresponding to C312, N313, W316 and R622 of SEQ ID NO: 1. Amino acid residues involved in substrate binding and substrate conversion in the C-site correspond to 5720, N721, H722, and N769 of SEQ ID NO: 1. The amino acids count starts from the initial Met residue of the pre-pro leader sequence, which is cleaved in the mature CDH. Corresponding amino acids are given in FIG. 1 herewith or FIG. 3 of WO2010/097462 A1 and can be determined by sequence comparison algorithms such as BLAST or Clustal (www.ebi.ac.uk/Tools/msa/clustalw2/). Corresponding amino acids are e.g. for the CDH of *C. thermophilus*: C310, N311, W314, R618, N718, *Chaetomium attrobrunneum*: C314, N315, W318, R624, N723, *Hypoxylon haematostroma*: C320, N321, W324, R638, N737, *Neurospora crassa*: C314, N315, W318, R623, N722 and *Stachybotris bisbii*: C312, N313, W316, R621, N721. Preferred *Corynascus thermophilus* modified amino acids are amino acids 309-318, 595-621 and 717-722, preferably of any one of amino acids 310, 311, 314, 618 and 718 of SEQ ID NO: 7, especially preferred a C314Y mutation in combination with either a W314L mutation or a W314R mutation.

The amino acid positions and modification to reduce maltose oxidation and/or increase glucose oxidation activity can be obtained by homology modeling using the crystal structure of *Phanerochaete chrysosporium* CDH (PDB database entry 1 kdg) as template and superimposition of the obtained models as well as docking studies. It is possible to use a CDH as template and by sequence comparison to obtain corresponding amino acids for modification to reduce maltose oxidation activity.

Possible modifications include (1) the exchange of small amino acids by bulkier ones to decrease the available space in the B-site of CDH for the bulkier and sterically demanding maltose molecule. Bulkiness correlates with molecular mass of the amino acids. Amino acids can be made bulkier by exchanging to the following amino acids beginning with the highest molecular mass: tryptophan>tyrosine>arginine>phenylalanine>histidine>methionine>glutamic acid>lysine>glutamine. These substituents are preferred modifications for all positions as identified, especially for amino acid corresponding to any one of amino acids 310-320, 342-347 or 599-625 of the *M. thermophilum* cellobiose dehydrogenase of SEQ ID NO: 1. Modifications in this order are especially preferred for positions corresponding to C312, N313 and/or N721 of SEQ ID NO: 1. 2) The exchange of amino acids forming stabilising interactions with the second glucose moiety of maltose in the B-site into amino acids exerting no or detrimental interactions and increase the $K_M$ value of maltose. E.g. amino acids corresponding to W316 and/or R622 of SEQ ID NO: 1 or further B-site amino acids as mentioned above, especially under (1), can be changed into alanine, valine, leucine, isoleucine, asparagine, glutamine or arginine. By such modifications also the binding of glucose in the B-site is weakened, which favours further transport to the C-site and the formation of the transition complex. 3) The exchange of the tryptophan residue corresponding to W316 in SEQ ID NO: 1 close to the second glucose moiety at the B-site by arginine, lysine, leucine or isoleucine to decrease the affinity of maltose.

Particularly preferred is a modification of at least one amino acid corresponding to any one of amino acids C312, N313, W316, R622 and/or N721 of the *M. thermophilum* cellobiose dehydrogenase of SEQ ID NO: 1, or any combination thereof.

An especially preferred modified CDH or its functional flavodehydrogenase domain, comprises at least a mutation corresponding to a C312Y, W316R, W316L, R622N, N721D mutation in SEQ ID NO: 1 or any combination thereof, preferably a C312Y mutation in combination with either a W316L mutation or a W316R mutation.

The modified CDH or its functional flavodehydrogenase domain may further comprise an amino acid modification increasing glucose oxidation activity. Several of the above mentioned modifications also achieve this goal.

The modified CDH or its functional flavodehydrogenase domain may be isolated by diafiltration, ion exchange chromatography and preferably being further purified by hydrophobic interaction chromatography. Preferably the CDH or the domain is recombinantly produced by *Pichia pastoris*.

The invention further provides a nucleic acid molecule encoding a modified CDH or its functional flavodehydrogenase domain as described above. Such nucleic acids are e.g. given in SEQ ID NOs. 2, 4, 6, 8, 10, 12 and 13. The inventive nucleic acid molecule encoding a cellobiose dehydrogenase having reduced maltose oxidation activity may comprise a nucleotide sequence of SEQ ID NOs 2, 4, 6, 8, 10, 12, or 13; or the open reading frame of SEQ ID NOs 2, 4, 6, 8, 10, 12, or 13; or a nucleotide sequence with at least 50%, preferably at least 55%, at least 60%, at least 65%, at least 70%, at least 75%, at least 80%, at least 85%, at least 90%, at least 95%, at least 98%, in particular preferred at least 99%, identity to SEQ ID NOs 2, 4, 6, 8, 10, 12, or 13 or the open reading frame of SEQ ID NOs 2, 4, 6, 8, 10, 12, or 13; a nucleotide sequence that hybridizes with any one of SEQ ID NO: 2, 4, 6, 8, 10, 12 or 13 under stringent condition; or a nucleotide portion of any of these sequences encoding the flavodehydrogenase domain portion; all of these further comprising a nucleotide mutation, substitution, deletion or insertion, preferably a codon mutation, substitution, deletion or insertion, that reduces the maltose oxidation activity of the encoded enzyme. Such mutations are given for the CDH polypeptide sequences as described above. Stringent conditions are as described in WO 2010/097462 A1, page 12, incorporated herein by reference. The nucleic acids, CDH or domains described herein may be isolated and/or purified.

Further provided is a method of producing a modified CDH or its functional flavodehydrogenase domain of the invention, comprising recombinantly expressing a nucleic acid molecule encoding said modified CDH or its functional flavodehydrogenase domain in a host cell.

In a further aspect the invention further provides an electrode comprising an immobilised cellobiose dehydrogenase or its functional flavodehydrogenase domain of the invention.

Preferably the electrode comprises an immobilised CDH in direct- or mediated electron transfer mode (Tasca et al. 2011a, Tasca et al. 2011b, Ludwig et al. 2010, Safina et al. 2010, Tasca et al 2010a, Tasca et al. 2010b) or an immobilised flavodehydrogenase domain in mediated electron transfer mode having a reduced maltose oxidation activity or a reduced maltose oxidation activity, preferably in combination with an increased glucose oxidation activity. As electrode any suitable surface for collecting electrons from CDH is understood. The electrode may be of any material suitable to immobilise the CDH, e.g. carbon such as graphite, pyrolytic graphite, glassy carbon, carbon nanotubes (single or multi-walled), carbon fibres, boron doped diamond, gold electrodes modified with promoters e.g., thiols or screen-printed electrodes. This is a non-exhaustive list of possible electrodes, which may e.g. contain other nanoparticles (gold, . . . ) to increase the specific surface area. Particular uses of the inventive electrodes are in the provision of biosensors, more specifically to glucose biosensors using the direct electron transfer properties (DET) of cellobiose dehydrogenase (CDH) or using mediated electron transfer properties (MET) to measure the glucose concentration at acidic, neutral, alkaline or, preferentially, physiological pH (in human body fluids, e.g., 7.4 in blood).

On the electrode, the CDH or the flavodehydrogenase domain may be immobilised by adsorption, preferably also physical entrapment in a polymer, complex formation, preferably via an additional complexing linker, covalent binding, in particular cross-linking, or ionic binding and/or the immobilized cellobiose dehydrogenase can be cross-linked, in particular by bifunctional agents, to increase stability or activity. It has been shown that cross-linking with bifunctional agents, such as agents with two reactive groups making a connection with the CDH, can stabilize the CDH and even increase its activity on graphite electrodes measurable by amperometric methods described herein. This advantage can lead to an increased sensitivity and lowering the detection limit for glucose. Such a cross-linking agent is e.g. glutaraldehyde or any other dialdehydes.

The electrodes might be used in form of a single electrode or electrode stacks.

The invention further provides a method of oxidizing glucose with the inventive CDH or flavin domain, especially in a method of detecting or quantifying glucose in a sample comprising the step of oxidizing glucose in said sample with a modified CDH or its functional flavodehydrogenase domain or an electrode as described herein and detecting or quantifying said oxidation, preferably wherein said sample comprises or is suspected of comprising maltose. The fluid sample may be any fluid which potentially comprises glucose, including blood, plasma, serum and other body fluids.

In a further aspect the present invention provides a glucose assay kit comprising the modified cellobiose dehydrogenase or its functional flavodehydrogenase domain or an electrode as described herein. The kit may in preferred embodiments also comprise auxiliary substances, like buffers, and containers such as a sample holding means and/or glucose standards. Glucose standards may be used to calibrate the assay.

The present invention is further illustrated by the following figures and examples without being restricted thereto.

FIGURES

FIG. 1 is a sequence alignment of amino acid sequences of the flavodehydrogenase domains ("flavin domains") of the CDHs from *Chaetomium atrobrunneum* (aa 253-831 of SEQ ID NO: 5), *Corynascus thermophilus* (aa 249-787 of SEQ ID NO: 7), *Hypoxylon haematostroma* (aa 263-839 of SEQ ID NO: 3), *Myriococcum thermophilum* (aa 251-828 of SEQ ID NO: 1), *Neurospora crassa* (aa 253-829 of SEQ ID NO: 11) and *Stachybotrys bisby* (aa 251-829 of SEQ ID NO: 9). Preferred mutation sites to improve glucose specificity are indicated by "*", especially preferred mutation sites are marked by "+".

FIG. 2 provides a glucose calibration curve of a sensor electrode featuring unmodified wild-type *M. thermophilum* CDH.

Figure 3:
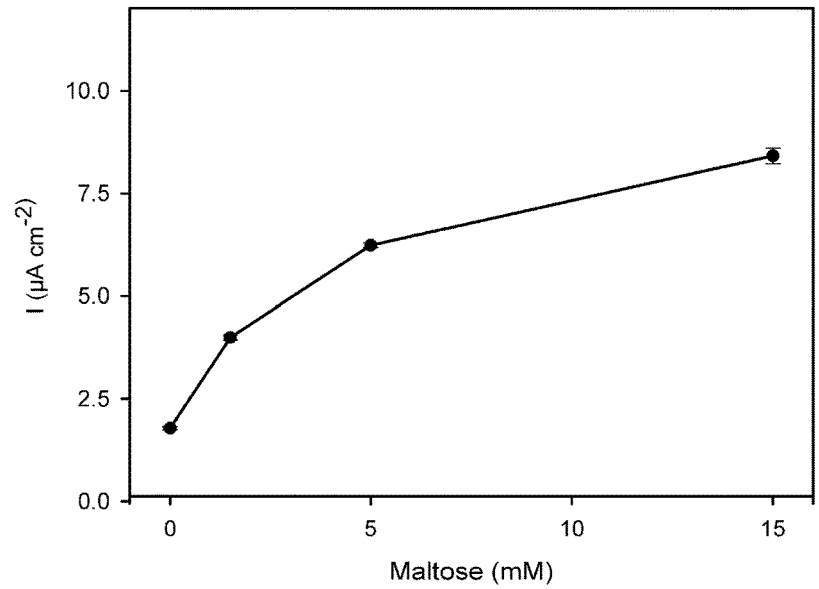

FIG. 3 shows the effect of spiking of a 5 mM glucose solution with different concentrations of maltose when using unmodified wild-type *M. thermophilum* CDH. The signal is maltose dependent.

Figure 4:
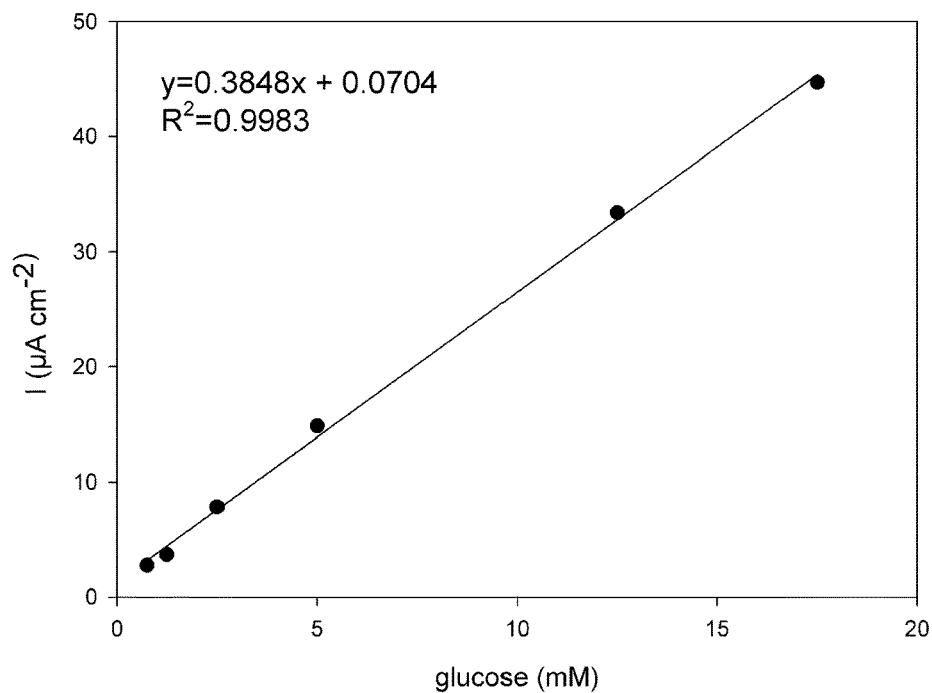

FIG. 4 provides a glucose calibration curve of a sensor electrode featuring *M. thermophilum* CDH variant C312Y.

Figure 5:
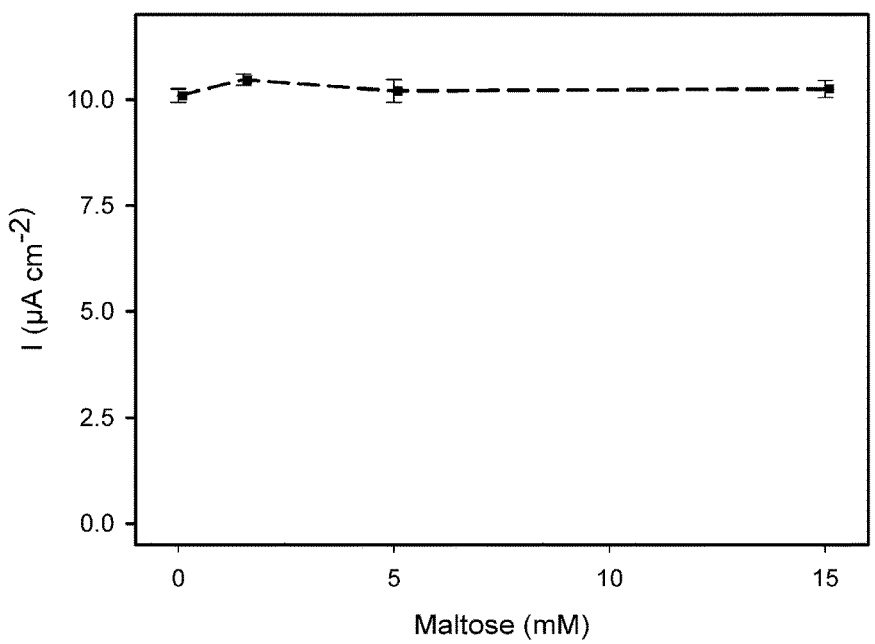

FIG. 5 shows the effect of spiking of a 5 mM glucose solution with different concentrations of maltose when using *M. thermophilum* CDH variant C312Y. The signal is independent on maltose concentrations.

Figure 6:
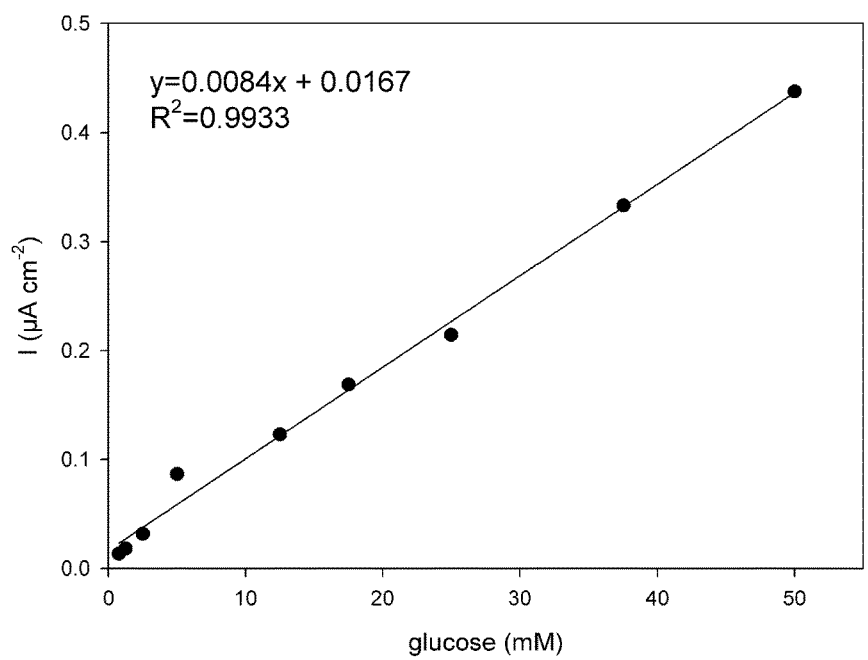

FIG. 6 provides a glucose calibration curve of a sensor electrode featuring *M. thermophilum* CDH variant W316R.

Figure 7:
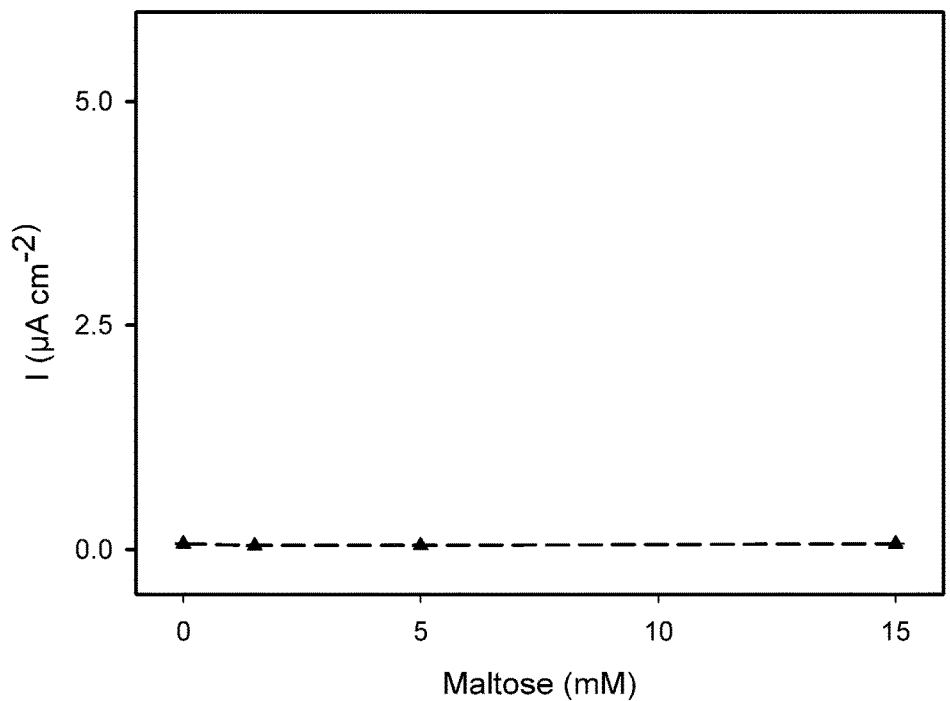

FIG. 7 shows the effect of spiking of a 5 mM glucose solution with different concentrations of maltose when using *M. thermophilum* CDH variant W316R. The signal is independent on maltose concentrations.

Figure 8:
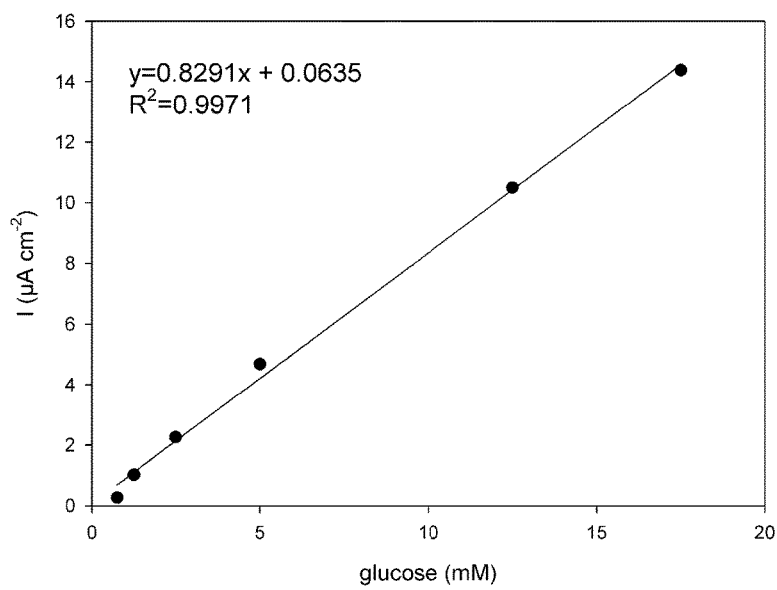

FIG. 8 provides a glucose calibration curve of a sensor electrode featuring *M. thermophilum* CDH double mutant variant C312Y/W316R.

Figure 9:
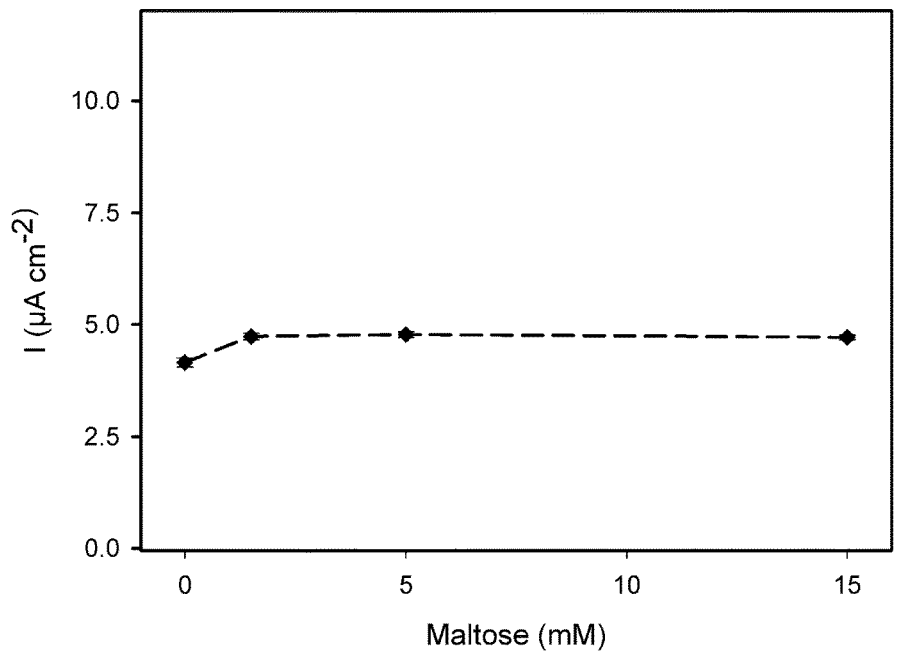

FIG. 9 shows the effect of spiking of a 5 mM glucose solution with different concentrations of maltose when using *M. thermophilum* CDH double mutant variant C312Y/W316R. The signal is independent on maltose concentrations.

EXAMPLES

Example 1

Materials

Chemicals used in buffers and fermentation media were commercial products and at least of analytical grade if not otherwise stated. Substrates for kinetic studies were cellobiose, lactose, maltose, glucose, 2,6-dichloroindophenol (DCIP) and cytochrome c from horse heart (cyt c) from Sigma-Aldrich in the highest grade of purity available. Buffers were prepared using water purified and deionised (18 M$\Omega$) with a Milli-Q system (Millipore, Bedford, Mass., USA).

Example 2

Enzymatic Activity Assays and Steady-State Kinetics

Enzyme activity was assayed at 30° C. using either the DCIP (Karapetyan et al., 2005 Journal of Biotechnology 121: 34-48) or cytochrome c (Canevascini et al., 1991, European Journal of Biochemistry 198: 43-52) as electron acceptor. Activities were assayed for 10 mM maltose and glucose at 30° C. in case of the MtCDH variants for both electron acceptors in 50 mM sodium acetate buffer pH 4.5 (TABLE 1) and for the CtCDH variants for DCIP in 50 mM sodium acetate buffer pH 5.5 and for cytochrome c in 50 mM sodium acetate buffer pH 7.5 (TABLE 2). Stock solutions of carbohydrates used for kinetic measurements were prepared in the respective buffer and allowed to stand overnight for mutarotation, while stock solutions of electron acceptors were prepared in water and immediately used. The reaction stoichiometry is 1 for the two-electron acceptor DCIP (1 mole of DCIP reduced per mole of carbohydrate oxidized), but 2 for the one-electron acceptor cytochrome c. Kinetic constants were calculated by fitting the observed data to the Henri-Michaelis-Menten equation or to the adapted model for substrate inhibition using nonlinear least-squares regression and the program SigmaPlot (Systat Software, San Jose, Calif., USA).

The protein concentration was determined with the Bradford assay.

Example 3

Protein Characterisation

The protein concentration was determined by the dye-staining method of Bradford using a pre-fabricated assay from Bio-Rad Laboratories Hercules, Calif., USA) and bovine serum albumin as standard according to the manufacturers recommendations.

For electrophoretic characterisation SDS-PAGE was carried out on a Hoefer SE 260 Mighty Small II vertical electrophoresis unit. Gels (10.5×10 cm; 10% T, 2.7% C) were cast and run according to the manufacturers' modifications of the Laemmli system. Protein bands on the SDS-PAGE were stained with silver, bands on the IEF gel with Coomassie blue R-250, according to the instructions.

Example 4

Generation of *Myriococcum thermophilum* CDH and *Corynascus thermophilus* CDH Variants by Site-Directed Mutagenesis The *M. thermophilum* CDH gene (EF492051, SEQ ID NO: 2) was codon-optimized for expression in *Pichia pastoris* according to the method described in Abad et al., 2010 and WO2010/097462 A1 (SEQ ID NO: 13) and synthesized by Gen-script (Piscataway, N.J., USA). cDNA encoding for *M. thermophilum* CDH was excised from the plasmid pMT-Sopt using EcoRI and NotI and cloned into the expression vector pPicZA along with its native signal sequence. Plasmid pCT1 was used as template for the amplification of the *C. thermophilus* CDH cDNA. Restriction enzymes BstBI and XbaI were used for cloning into the expression vector pPicZB along with its native signal sequence. Mutants of *M. thermophilum* CDH: C312Y, N313S, W316L, W316R, R622N, N721D, C312Y/W316L, C312Y/W316R and *C. thermophiles* CDH C310Y were prepared by a two step mutagenesis approach using PCR and DpnI (Li et al., 2002). The mutations were confirmed by sequencing (LGC Genomics, Berlin, Germany). SacI linearized expression plasmids were transformed into electrocompetent X-33 cells and transformants were selected on YPD Zeocin plates (1 mg $L^{-1}$).

Example 5

Production of *Corynascus thermophilus* Flavin Domain

Sequence encoding for the flavin domain without its haem domain was reamplified by PCR and the resulting DNA fragment cloned into the yeast expression vector pPicZB along with its native signal sequence. The construct was confirmed by sequencing. SacI linearized expression plasmids were transformed into electrocompetent X-33 cells and transformants were selected on YPD Zeocin plates (1 mg L-1).

Example 6

Production of Recombinant CDH

Recombinant wild-type CDH as well as variants were produced in 1 L baffled flasks. Precultures were grown overnight in 30 mL of YPD medium at 30° C. and 120 rpm. After approximately 18 hours the precultures were transferred into 1 L baffled flasks containing 200 mL BMGY medium without methanol. Induction with methanol was started immediately using a multichannel peristaltic pump (Minipuls Evolution, Gilson, Middleton, Wis., USA). Each flask was supplied eight times a day with methanol yielding a total concentration of 2% (v/v) methanol per day. Increase in activity was monitored using the DCIP and the cytochrome c enzyme assays. Cultivation was stopped at day five of methanol induction, cells removed by centrifugation (4000 rpm, 20 min) and the supernatant set to a final ammonium sulfate concentration of 20%.

Example 7

Purification of Recombinant CDH

Enzymes were purified to homogeneity in a two-step purification. The sample was loaded on a 20 mL PHE Sepharose FF column (HR26/20) equilibrated with 50 mM Na-acetate buffer pH 5.5 containing 20% ammonium sulfate. Proteins were eluted by increasing the concentration of the elution buffer (50 mM Na-acetate buffer pH 5.5) from 0 to 100% in 5 column volumes and fractions containing CDH activity were pooled. After diafiltration with a polyethersulfone flat-stack cross flow module with a cut-off of 10 kDa (Viva Flow 50, Sartorius, Göttingen, Germany) until conductivity of 5 mS $cm^{-1}$ in 20 mM Na-acetate pH 5.5 the samples were loaded on a 20 mL Q-Source column (HR26/20) equilibrated with a 20 mM Na-acetate buffer pH 5.5. CDH was eluted by increasing the concentration of the elution buffer (50 mM Na-acetate buffer pH 5.5 containing 0.5 M NaCl) from 0 to 100% in 50 column volumes. Fractions were tested for CDH activity and pooled according to the highest Reinheitszahl (RZ, calculated from the absorbance ratio 420 nm/280 nm). Purified enzymes were concentrated and diafiltered in 50 mM citrate buffer, pH 5.5, aliquoted and kept at 4° C. for further use.

Example 8

Electrochemical Measurements

A three electrode flow through amperometric wall jet cell was used (BASi LCEC flow cell, radial flow, West Lafayette, Ind., USA) and contained homemade working electrode (graphite electrode modified with CDH), a reference electrode (Ag|AgCl vs. 3 M NaCl, RE-6, BASi) and a counter electrode block (BASi), connected to a potentiostat (μSTAT 200, Dropsens, Oviedo, Spain). The enzyme modified electrode was pressfitted into a Teflon holder and screwed onto the counter electrode block, which kept a constant distance (ca. 1 mm) from the inlet nozzle. The system was controlled by the Dropview-program (Dropsens). The electrochemical cell was connected on-line to a single line flow injection (FI) system, in which the carrier flow was maintained at a constant flow rate of 0.5 mL $min^{-1}$ by a peristaltic pump (Minipuls 2, Gilson). The injector was a mechanically controlled six-port valve (Rheodyne, Cotati, Calif., USA), and the injection loop volume was 20 μL. The enzyme, CDH, was immobilized through simple chemo-physical adsorption onto the surface of solid spectroscopic graphite electrodes (FP-254, OD 3.05 mm, Schunk Materials, Heuchelheim, Germany). The electrode was cut and polished on wet emery paper (EasyCUT, P600), afterwards sonicated and carefully rinsed with HQ water and dried. Enzyme-modified electrodes were prepared by adsorbing a mixture of 3 μL enzyme solution (5 mg mL-1) with 2 μL (Poly (vinylpyridine)-[osmium-(N,N'-methylated-2,2'-biimidalzole)$_3$]$^{2+/3+}$ (10 mg·$ml^{-1}$) (Mao et al., 2003) and 1 μL poly(ethylene glycol) (400) diglycidylether (PEGDGE, 10 mg·$ml^{-1}$) on top of the graphite electrode. The enzyme electrode was dried at room temperature and stored overnight at 4° C. for complete cross-linking reaction. Before use, the electrode was thoroughly rinsed with HQ water in order to remove any weakly adsorbed enzyme and plugged into the wall jet cell already containing buffer (PBS buffer pH 7.4). Then, a potential of 0 mV vs. Ag|AgCl was applied until a stable background current was obtained before any substrate injection into the flow system. The current densities were calculated with respect to the geometric electrode area of 0.0731 cm². The dispersion factor of the flow system used including the wall jet cell, determined according to the Ruzicka and Hansen relationship, by dividing the steady state current registered for a 5 mM ferrocyanide solution with that of the peak current for the injected sample having an equal concentration of ferrocyanide and using an applied potential of +300 mV. In our case, for a 1 mm distance between electrode and inlet nozzle and 0.5 mL min$^{-1}$ flow rate, the dispersion factor D was equal to 1.99 (Ruzicka and Hansen, 1988). The buffers were prepared using HQ-water (0.055 μScm$^{-1}$) purified with a SG Ultra Clear Basic UV (SG-Wasseraufbereitung, Barsbuttel, Germany). All buffers were degassed before use to prevent microbubbles in the flow system.

Example 9

Mutated CDH from *Myriococcum thermophilum*—Reduced Maltose Activity

CDH from *M. thermophilum* oxidises maltose (Harreither et al., 2007), which has negative side effects on the glucose detection accuracy if maltose is present. To reduce the activity with maltose, *M. thermophilum* CDH was used as a protein scaffold for which the maltose activity was greatly reduced. The enzyme variants C312Y, N313S, W316L, W316R, R622N and N721D were heterologously produced in *P. pastoris* according to the explained routines and compared to the recombinant wild-type CDH from *M. thermophilum*. The molecular weights did not differ significantly from the native enzyme produced by the fungus. A kinetic characterisation was performed and the results given in Table 1.

TABLE 1

Specific activities for 10 mM maltose and 10 mM glucose for modified *M. thermophilum* CDH enzyme variants.

| | DCIP act.$^a$ (U mg$^{-1}$) | | ratio |
|---|---|---|---|
| | 10 mM Maltose | 10 Mn Glucose | Glucose/Maltose |
| wt | 0.123 | 0.0669 | 0.54 |
| C312Y | 0.1124 | 0.3787 | 3.37 |
| N313S | 0.2228 | 0.0784 | 0.35 |
| W316L | 0.0196 | 0.0238 | 1.22 |
| W316R | 0 | 0 | 0 |
| R622N | 0.0445 | 0.0516 | 1.16 |
| N721D | 0.476 | 0.123 | 2.58 |
| C312Y/W316L | 0.0047 | 0.0712 | 14.99 |
| C312Y/W316R | 0.0016 | 0.0303 | 18.88 |
| C312Y/N721D | 0.0147 | 0.3362 | 22.87 |

$^a$activity was measured at pH 4.5.

The obtained specific activities show unequivocally that maltose conversion alone or in the presence of glucose is tremendously decreased with the generated enzyme variants. The highest ratio of glucose/maltose activity indicates the enzyme variants with the highest suppression of maltose activity.

To further investigate the effect of the mutations in the *M. thermophilum* variants a full characterization of steady-state constants was performed (Table 2).

TABLE 2

Apparent kinetic constants for carbohydrates (electron donors) for *M. thermophilum* CDH variants.

| | Maltose* | | | Glucose* | | |
|---|---|---|---|---|---|---|
| | $K_M$ (mM) | $k_{cat}$ (s$^{-1}$) | $k_{cat}/K_M$ (M$^{-1}$ s$^{-1}$) | $K_M$ (mM) | $K_{cat}$ (s$^{-1}$) | $k_{cat}/K_M$ (M$^{-1}$ s$^{-1}$) |
| wt | 6.8 | 0.32 | 47 | 387 | 4.8 | 12 |
| C312Y | 138 | 0.48 | 3.5 | 192 | 9.6 | 50 |
| N313S | 52 | 1.3 | 25 | 765 | 6.8 | 8.8 |
| W316L | 225 | 0.59 | 2.6 | ~3500 | ~9.9 | 2.8 |
| W316R | 1400 | 0.12 | 0.09 | ~3500 | ~1.2 | 0.34 |
| R622N | 247 | 1.3 | 5.2 | ~2100 | ~13.1 | 6.0 |
| N721D | 6.1 | 0.08 | 13.2 | 331 | 1.9 | 5.9 |
| C312Y/W316L | ~1400 | ~0.92 | 0.62 | 490 | 6.4 | 13 |
| C312Y/W316R | ~16000 | ~2.7 | 0.17 | 700 | 4.3 | 6.2 |
| C312Y/N721D | 110 | 0.09 | 0.81 | 150 | 2.0 | 13.3 |

$^a$activity was measured at pH 4.5 with the DCIP assay.
~values are only estimated by non linear regression The constants in Table 2 show in more detail that maltose oxidation activity is suppressed in *M. thermophilum* CDH variants, especially in the double variants, whereas glucose turnover is stabilized by the mutation C291Y.

Example 10

Mutated CDH from *Corynascus thermophilus*—Reduced Maltose Activity

CDH from *C. thermopilus* was also found to oxidise maltose (Harreither et al., 2011). To reduce the activity with maltose, *C. thermophilus* CDH was used as a protein scaffold for which the maltose activity was greatly reduced. The enzyme variant C312Y was produced heterologously in *P. pastoris* according to the explained routines and compared to the recombinant wild-type CDH from *C. thermophilus*. The molecular weight did not differ significantly from the native enzyme produced by the fungus. A kinetic characterisation was performed (Table 3).

TABLE 3

Specific activities for 10 mM maltose and 10 mM glucose (electron donors) for *C. thermophiles* CDH wild-type and variant.

| | DCIP act. (U mg$^{-1}$) | | ratio |
|---|---|---|---|
| | 10 mM Maltose | 10 mM Glucose | Glucose/Maltose |
| wt | 0.26 | 0.30 | 1.5 |
| C310Y | 0.11 | 2.86 | 26 |

$^a$activity was measured at pH 5.5.

The obtained specific activity and the activity ratio show unequivocally that maltose conversion is tremendously decreased in the variant.

To further investigate the effect of the mutations in the *C. thermophilus* variant a full characterization of steady-state constants was performed (Table 4).

TABLE 4

Apparent kinetic constants for carbohydrates (electron donors) for *C. thermophilus* CDH wild-type and variant C310Y.

| | Maltose[a] | | | Glucose[a] | | |
|---|---|---|---|---|---|---|
| | $K_M$ (mM) | $k_{cat}$ (s$^{-1}$) | $k_{cat}/K_M$ (M$^{-1}$ s$^{-1}$) | $K_M$ (mM) | $k_{cat}$ (s$^{-1}$) | $k_{cat}/K_M$ (M$^{-1}$ s$^{-1}$) |
| wt | 4.08 | 0.50 | 120 | 86.7 | 4.09 | 170 |
| C310Y | 80.0 | 0.95 | 12 | 37.5 | 19.67 | 524.5 |

[a]activity was measured at pH 5.5 with the DCIP assay.

The constants given in Table 4 show in more detail that maltose oxidation activity is strongly discriminated in the variant, whereas glucose turnover is increased by the variant C310Y.

Example 11

Mutated Flavodehydrogenase Domain from *Corynascus thermophilus*—Reduced Maltose Activity To reduce the activity with maltose, *C. thermophilus* flavodehydrogenase domain was used as a protein scaffold for which the maltose activity was greatly reduced. The enzyme variant C310Y was produced heterologeously in *P. pastoris* according to the explained routines and compared to the recombinant wild-type flavodehydrogenase domain from *C. thermophilus*. A kinetic characterisation was performed (Table 5).

TABLE 5

Specific actitivies for 10 Mm maltose and 10 Mm glucose (electron donors) for *C. thermophilus* CDH wild-type flavodehydrogenase domain and variant C310Y.

| | DCIP act. (U mg$^{-1}$) ratio | | |
|---|---|---|---|
| | 10 mM Maltose | 10 mM Glucose | Glucose/Maltose |
| wtDH | 0.69 | 0.72 | 1.0 |
| C310YDH | 0.175 | 4.7 | 26.9 |

[a]activity was measured at pH 5.5.

The obtained specific activity and the activity ratio show unequivocally that maltose conversion is tremendously decreased in the variant.

To further investigate the effect of the mutations in the *C. thermophilus* flavodehydrogenase domain variant a full characterization of steady-state constants was performed (Table 6).

TABLE 6

Apparent kinetic constants for carbohydrates (electron donors) for *C. thermophilus* CDH wild-type flavodehydrogenase domain and variant C310Y.

| | Maltose[a] | | | Glucose[a] | | |
|---|---|---|---|---|---|---|
| | $K_M$ (mM) | $k_{cat}$ (s$^{-1}$) | $k_{cat}/K_M$ (M$^{-1}$ s$^{-1}$) | $K_M$ (mM) | $k_{cat}$ (s$^{-1}$) | $k_{cat}/K_M$ (M$^{-1}$ s$^{-1}$) |
| wt | 2.89 | 0.86 | 296 | 111.2 | 8.8 | 79.1 |
| C310Y | 51.86 | 0.69 | 13.3 | 37.1 | 17.6 | 474.4 |

[a]activity was measured at pH 5.5 with the DCIP assay.

The constants given in Table 4 show in more detail that maltose oxidation activity is strongly discriminated in the variant, whereas glucose turnover is increased by the variant C310Y.

Example 12

Mutated CDH from *Myriococcum thermophilum*—Electrode Performance

To test the modified *M. thermophilum* CDHs (variants) in a biosensor, three of them and the wild-type CDH were selected, immobilized on graphite electrodes and the current responses in different concentrations of glucose and maltose measured. In Table 7, a summary of the sensor parameters for glucose is given as determined from FIGS. 2, 4, 6 and 8. FIGS. 3, 5, 7 and 9 show the influence of different maltose concentrations on glucose measurements. In contrast to the wild-type CDH, no significant influence of maltose on glucose measurements could be detected in the measurements with the CDH variants.

TABLE 7

Analytical parameters for glucose for the CDH modified carbon electrode.

| Variant | Sensitivity (µA cm$^{-2}$ mM$^{-1}$) | Detection limit (mM) | Linear range (mM) |
|---|---|---|---|
| wt | 0.33 ± 0.07 | 1.5 | 1-50 |
| C312Y | 2.1 ± 0.65 | 0.1 | 0.1-20 |
| W316R | 0.007 ± 0.002 | 75 | n.d. |
| C312Y/W316R | 0.75 ± 0.11 | 0.75 | 0.75-20 |

REFERENCES

Abad et al. (2010) Microb Cell Fact 9:24.

Hallberg et al. (2002) Journal of Molecular Biology 315: 421-434

Harreither et al. (2007) Electroanal., 19: 172-180.

Harreither et al. (2011) Appl. Environ. Microbiol. 77:1804-1815.

Henriksson et al. (1998) Biochem. Biophys. Acta 1383:48-54

Li and Mullins (2002) Methods in Molecular Biology 182: 19-87

Ludwig et al. (2010) Chem. Phys. Chem. 11:2674-2697

Mao et al. (2003) JACS. 125(16): 4951-4957

Ruzicka, J.; Hansen, E. H. Flow Injection Analysis, 1988, 2nd ed. Wiley, New York Sagina et al. (2010) Electrochimica Acta 55: 7690-7695.

Sygmund et al. (2009) New Biotechnology 225: 115.

Tasca et al. (2010) Bioelect. 25:1710-1716.

Tasca et al. (2010b) Bioelect. 25:1710-1716.

Tasca et al. (2011) Anal. Chem. 83:3042-3049.

Tasca et al. (2011b). Analyst 136:2033-2036.

Zámocký et al. (2006) Curr. Protein Pept. Sci. 7:255-280.

Zamocky et al. (2008) Protein Expression and Purification 59 (2): 258-265.

The invention claimed is:

1. A polypeptide comprising a modified flavodehydrogenase domain, which comprises a modification of at least one amino acid corresponding to any one of amino acids C312, N313, W316, R622 and/or N721 of SEQ ID NO: 1, or any combination thereof; wherein the flavodehydrogenase domain has an amino acid sequence of at least 80% sequence identity to a sequence selected from amino acids 251-828 of SEQ ID NO: 1, amino acids 263-839 of SEQ ID NO: 3, amino acids 253-831 of SEQ ID NO: 5, amino acids 249-787 of SEQ ID NO: 7, amino acids 251-829 of SEQ ID NO: 9, or amino acids 253-829 of SEQ ID NO: 11.

2. The polypeptide of claim 1, comprising at least a mutation corresponding to a C312Y, W316R, W316L, R622N, N721D mutation in SEQ ID NO: 1 or any combination thereof.

3. The polypeptide of claim 2, comprising a C312Y mutation in combination with either a W316L mutation or a W316R mutation.

4. The polypeptide of claim 1, wherein the flavodehydrogenase domain corresponds to an unmodified cellobiose dehydrogenase (CDH), said unmodified CDH being a CDH of *Myriococcum therrnophilum, Corynascus thermophilus, Chaetomium atrobrunneum, Hypoxylon haematostroma, Neurospora crassa* or *Stachybotrys bisby.*

5. The polypeptide of claim 1, wherein the $K_M$ value of the modified flavodehydrogenase domain for a maltose oxidation reaction is above 50 mM.

6. The polypeptide of claim 5, wherein the $K_M$ value can be determined with the CDH or said domain being immobilized on an electrode.

7. An electrode comprising an immobilized polypeptide of claim 1.

8. The electrode of claim 7, wherein the polypeptide is immobilized by adsorption, complex formation, or covalent or ionic linkage.

9. The electrode of claim 8, wherein the polypeptide is immobilized by a complexing linker.

10. The electrode of claim 7, wherein the immobilized polypeptide is cross-linked in a manner increasing stability or activity during use.

11. The electrode of claim 8, wherein the polypeptide is cross-linked by a bifunctional crosslinking agent.

12. A method of detecting or quantifying glucose in a sample, comprising:
oxidizing glucose in said sample with a polypeptide of claim 1; and
detecting or quantifying said oxidation.

13. The method of claim 12, wherein said sample is a blood, blood plasma, or blood serum sample.

* * * * *

UNITED STATES PATENT AND TRADEMARK OFFICE
CERTIFICATE OF CORRECTION

PATENT NO. : 10,184,115 B2
APPLICATION NO. : 14/383848
DATED : January 22, 2019
INVENTOR(S) : Roland Ludwig et al.

It is certified that error appears in the above-identified patent and that said Letters Patent is hereby corrected as shown below:

In the Claims

Claim 4, Column 55, Line 64:
Delete "*therrnophilum*" and replace with -- *thermophilum* --.

Signed and Sealed this
Sixteenth Day of April, 2019

Andrei Iancu
*Director of the United States Patent and Trademark Office*

SEQUENCE LISTING

<160> NUMBER OF SEQ ID NOS: 13

<210> SEQ ID NO 1
<211> LENGTH: 828
<212> TYPE: PRT
<213> ORGANISM: Myriococcum thermophilum

<400> SEQUENCE: 1

```
Met Arg Thr Ser Ser Arg Leu Ile Gly Ala Leu Ala Ala Leu Leu
1               5                   10                  15

Pro Ser Ala Leu Ala Gln Asn Asn Val Pro Asn Thr Phe Thr Asp Pro
            20                  25                  30

Asp Ser Gly Ile Thr Phe Asn Thr Trp Gly Leu Asp Glu Asp Ser Pro
            35                  40                  45

Gln Thr Gln Gly Gly Phe Thr Phe Gly Val Ala Leu Pro Ser Asp Ala
50                  55                  60

Leu Thr Thr Asp Ala Ser Glu Phe Ile Gly Tyr Leu Lys Cys Ala Arg
65                  70                  75                  80

Asn Asp Glu Ser Gly Trp Cys Gly Ile Ser Leu Gly Gly Pro Met Thr
                85                  90                  95

Asn Ser Leu Leu Ile Thr Ala Trp Pro His Glu Asp Thr Val Tyr Thr
            100                 105                 110

Ser Leu Arg Phe Ala Thr Gly Tyr Ala Met Pro Asp Val Tyr Glu Gly
            115                 120                 125

Asp Ala Glu Ile Thr Gln Val Ser Ser Ser Val Asn Ser Thr His Phe
        130                 135                 140

Ser Leu Ile Phe Arg Cys Lys Asn Cys Leu Gln Trp Ser His Gly Gly
145                 150                 155                 160

Ser Ser Gly Gly Ala Ser Thr Ser Gly Gly Val Leu Val Leu Gly Trp
                165                 170                 175

Val Gln Ala Phe Asp Asp Pro Gly Asn Pro Thr Cys Pro Glu Gln Ile
            180                 185                 190

Thr Leu Gln Gln His Asp Asn Gly Met Gly Ile Trp Gly Ala Gln Leu
            195                 200                 205

Asn Thr Asp Ala Ala Ser Pro Ser Tyr Thr Asp Trp Ala Ala Gln Ala
        210                 215                 220

Thr Lys Thr Val Thr Gly Asp Cys Glu Gly Pro Thr Glu Thr Ser Val
225                 230                 235                 240

Val Gly Val Pro Val Pro Thr Gly Val Ser Phe Asp Tyr Ile Val Val
                245                 250                 255

Gly Gly Gly Ala Gly Gly Ile Pro Ala Ala Asp Lys Leu Ser Glu Ala
            260                 265                 270

Gly Lys Ser Val Leu Leu Ile Glu Lys Gly Phe Ala Ser Thr Ala Asn
        275                 280                 285

Thr Gly Gly Thr Leu Gly Pro Glu Trp Leu Glu Gly His Asp Leu Thr
    290                 295                 300

Arg Phe Asp Val Pro Gly Leu Cys Asn Gln Ile Trp Val Asp Ser Lys
305                 310                 315                 320

Gly Ile Ala Cys Glu Asp Thr Asp Gln Met Ala Gly Cys Val Leu Gly
                325                 330                 335

Gly Gly Thr Ala Val Asn Ala Gly Leu Trp Phe Lys Pro Tyr Ser Leu
            340                 345                 350

Asp Trp Asp Tyr Leu Phe Pro Asp Gly Trp Lys Tyr Asn Asp Val Gln
        355                 360                 365
```

```
Pro Ala Ile Asn Arg Ala Leu Ser Arg Ile Pro Gly Thr Asp Ala Pro
    370                 375                 380

Ser Thr Asp Gly Lys Arg Tyr Tyr Gln Glu Gly Phe Glu Val Leu Ser
385                 390                 395                 400

Lys Gly Leu Ala Ala Gly Gly Trp Thr Ser Val Thr Ala Asn Asn Ala
                405                 410                 415

Pro Asp Lys Lys Asn Arg Thr Phe Ala His Ala Pro Phe Met Phe Ala
            420                 425                 430

Gly Gly Glu Arg Asn Gly Pro Leu Gly Thr Tyr Phe Gln Thr Ala Lys
        435                 440                 445

Lys Arg Asn Asn Phe Asp Val Trp Leu Asn Thr Ser Val Lys Arg Val
    450                 455                 460

Ile Arg Glu Gly Gly His Ile Thr Gly Val Glu Val Glu Pro Phe Arg
465                 470                 475                 480

Asp Gly Gly Tyr Glu Gly Ile Val Pro Val Thr Lys Val Thr Gly Arg
                485                 490                 495

Val Ile Leu Ser Ala Gly Thr Phe Gly Ser Ala Lys Ile Leu Leu Arg
                500                 505                 510

Ser Gly Ile Gly Pro Glu Asp Gln Leu Glu Val Val Ala Ala Ser Glu
            515                 520                 525

Lys Asp Gly Pro Thr Met Ile Gly Asn Ser Ser Trp Ile Asn Leu Pro
    530                 535                 540

Val Gly Tyr Asn Leu Asp His Leu Asn Thr Asp Thr Val Ile Ser
545                 550                 555                 560

His Pro Asp Val Val Phe Tyr Asp Phe Tyr Glu Ala Trp Asp Asp Pro
                565                 570                 575

Ile Glu Ser Asp Lys Asn Ser Tyr Leu Glu Ser Arg Thr Gly Ile Leu
            580                 585                 590

Ala Gln Ala Ala Pro Asn Ile Gly Pro Met Phe Trp Glu Glu Ile Val
        595                 600                 605

Gly Ala Asp Gly Ile Val Arg Gln Leu Gln Trp Thr Ala Arg Val Glu
    610                 615                 620

Gly Ser Leu Gly Ala Pro Asn Gly His Thr Met Thr Met Ser Gln Tyr
625                 630                 635                 640

Leu Gly Arg Gly Ala Thr Ser Arg Gly Arg Met Thr Ile Thr Pro Ser
                645                 650                 655

Leu Thr Thr Ile Val Ser Asp Val Pro Tyr Leu Lys Asp Pro Asn Asp
            660                 665                 670

Lys Glu Ala Val Ile Gln Gly Ile Ile Asn Leu Gln Asn Ala Leu Gln
        675                 680                 685

Asn Val Ala Asn Leu Thr Trp Leu Phe Pro Asn Ser Thr Ile Thr Pro
    690                 695                 700

Arg Glu Tyr Val Glu Ser Met Val Val Ser Pro Ser Asn Arg Arg Ser
705                 710                 715                 720

Asn His Trp Met Gly Thr Asn Lys Leu Gly Thr Asp Asp Gly Arg Lys
                725                 730                 735

Gly Gly Ser Ala Val Val Asp Leu Asp Thr Arg Val Tyr Gly Thr Asp
            740                 745                 750

Asn Leu Phe Val Ile Asp Ala Ser Ile Phe Pro Gly Val Pro Thr Thr
        755                 760                 765

Asn Pro Thr Ser Tyr Ile Val Val Ala Ala Glu His Ala Ser Ser Arg
    770                 775                 780

Ile Leu Ala Leu Pro Asp Leu Glu Pro Val Pro Lys Tyr Gly Gln Cys
```

```
                785                 790                 795                 800
          Gly Gly Arg Glu Trp Thr Gly Ser Phe Val Cys Ala Asp Gly Ser Thr
                              805                 810                 815

Cys Glu Tyr Gln Asn Glu Trp Tyr Ser Gln Cys Leu
                          820                 825

<210> SEQ ID NO 2
<211> LENGTH: 2487
<212> TYPE: DNA
<213> ORGANISM: Myriococcum thermophilum

<400> SEQUENCE: 2
atgaggacct cctctcgttt aatcggagcc cttgcggcgg cacttttgcc gtctgccctt      60
gcccagaaca atgtcccgaa tactttttacc gaccctgact cgggcatcac cttcaacacg     120
tggggtctcg acgaggattc tccccagact cagggcggtt tcaccttcgg cgttgccctg     180
ccctctgatg ccctcacaac cgacgcctcg gaatttatcg gttacttgaa atgcgcaagg     240
aatgatgaga gcggttggtg tggcattttcc cttggcgggc ctatgaccaa ctcgctcctc     300
atcacagcct ggccgcacga ggacacggtc taccagtc ttcggttcgc gaccggttac     360
gccatgccga tgtctacga gggggacgcc gagattaccc aggtctcttc ctctgttaat     420
tcgacgcact tcagtctcat cttcaggtgc aagaactgcc tgcaatggag ccacggcggc     480
tcctccggcg cgcctctac ctcgggcggc gtgttggtac tcggctgggt tcaggcattc     540
gacgatcccg gcaatccaac ctgccccgag cagatcacac tccagcagca cgacaacggc     600
atgggtatct ggggtgccca gctcaacacg gatgctgcca gcccgtccta cactgactgg     660
gccgcccagg ctaccaagac cgtcaccggt gactgcgagg ccccaccga cttctctgtc     720 gtcggcgtcc ccgttccgac gggtgtctcg ttcgattata ttgttgtcgg cggcggcgcc     780
gggggcatcc ccgcagctga caagctcagc gaggccggca agagtgtgtt gctcatcgag     840
aagggctttg cttcgaccgc aaacaccgga ggtactctcg gccctgaatg gcttgagggc     900
catgatctga cccgcttcga cgtgccgggt ctgtgcaacc agatctgggt cgattccaag     960
gggatcgctt gcgaggatac cgaccagatg gctggctgtg ttctcggcgg cggcaccgcc    1020
gtgaatgctg gcctgtggtt caagccctac tcgctcgact gggactacct cttccccgat    1080
ggttggaagt acaatgacgt ccagcctgcc atcaaccgcg ccctctcgcg catcccaggc    1140
accgacgccc cttctaccga cggaaagcgc tactaccagg agggttttga ggtcctctcc    1200
aagggcctgg ccgccggcgg ctggacctca gtcacggcca ataatgcgcc cgacaagaag    1260
aaccgcacct tcgcccatgc tccccttcatg tttgccggcg cgagcgcaa tggccctctg    1320 ggtacctact tccagactgc caagaagcgc aacaatttcg atgtctggct caacacgtcg    1380
gtcaagcgcg tcatccgtga gggtggccac atcaccggcg tcgaggtcga ccgttccgt    1440 gacggtggtt acgagggcat tgtccccgtc accaaggtta ccggccgcgt tatcctgtct    1500
gccggcacct tcgcagtgc aaagattctg ttaaggagcg tattgggccc ggaagatcag    1560
ctagaagttg tcgcggcctc cgagaaggac ggccctacca tgatcggcaa ctcgtcctgg    1620
atcaacctgc tgtcgggta caacctcgat gaccatctca acaccgacac agtcatctcc    1680
caccccgatg tcgtgttcta cgactttac gaggcgtggg atgatccatt cgagtctgac    1740
aagaatagct atctcgaatc gcgtacgggc atcctcgccc aagccgctcc caacattggc    1800
cctatgttct gggaagagat cgtgggcgcg acggcatcc ttcgccagct ccagtggact    1860
gcccgtgtcg agggtagcct gggcgctccc aacggccaca ctatgaccat gtcgcagtac    1920
```

```
cttggccgtg gtgccacctc acgcggccgc atgaccatca ccccgtctct gacgactatc    1980
gtctcagacg tgccttacct caaagacccc aacgacaagg aggctgtcat ccaaggcatc    2040
atcaacctgc agaacgccct tcagaacgtc gccaacctga cttggctctt ccccaactct    2100
accattacgc cgcgcgaata cgttgagagc atggtcgtct ccccgagcaa ccggcggtcc    2160
aaccactgga tgggcaccaa caagctcggt accgacgacg ggcggaaggg tggctccgct    2220
gtcgtcgacc tcgacaccag ggtctacggt actgacaacc tcttcgtcat cgacgcctcc    2280
atcttccccg gcgtgcccac cacgaatcct acttcgtaca tcgtggtagc ggcagagcac    2340
gcttcgtccc gcatcctcgc cctgcccgac ctcgagcccg tccccaagta cggccagtgt    2400
ggcggtcgcg aatggaccgg tagcttcgtc tgcgccgatg gttccacgtg cgagtaccag    2460
aatgagtggt actcgcagtg cttgtga                                       2487
```

<210> SEQ ID NO 3
<211> LENGTH: 845
<212> TYPE: PRT
<213> ORGANISM: Hypoxylon haematostroma

<400> SEQUENCE: 3

```
Met Gly Arg Leu Gly Ser Leu Ala Lys Leu Leu Ala Val Gly Leu
1               5                   10                  15

Asn Val Gln Gln Cys Phe Gly Gln Asn Gly Pro Pro Thr Pro Tyr Thr
            20                  25                  30

Asp Ser Glu Thr Gly Ile Thr Phe Ala Thr Trp Ser Val Pro Asp Arg
        35                  40                  45

Ala Glu Gly Gly Asn Gly Leu Ala Pro Trp Gly Leu Thr Phe Gly
    50                  55                  60

Val Ala Leu Pro Glu Asn Ala Leu Thr Thr Asp Ala Thr Glu Leu Ile
65                  70                  75                  80

Gly Tyr Leu Lys Cys Gly Ser Asn Gly Thr Thr Thr Asp Ala Trp Cys
                85                  90                  95

Gly Leu Ser Phe Gly Gly Pro Met Thr Asn Ser Leu Leu Met Ala
            100                 105                 110

Trp Pro His Glu Asp Glu Ile Leu Thr Ser Phe Arg Phe Ala Ser Gly
        115                 120                 125

Tyr Thr Arg Pro Asp Leu Tyr Thr Gly Asp Ala Lys Leu Thr Gln Ile
    130                 135                 140

Ser Ser Thr Ile Asp Lys Asp His Phe Thr Leu Ile Phe Arg Cys Gln
145                 150                 155                 160

Asn Cys Leu Ala Trp Asn Gln Asp Gly Ala Ser Gly Ser Ala Ser Thr
                165                 170                 175

Ser Ala Gly Ser Leu Ile Leu Gly Trp Ala Ser Ala Leu Arg Ala Pro
            180                 185                 190

Thr Asn Ala Gly Cys Pro Ala Glu Ile Asn Phe Asn Phe His Asn Asn
        195                 200                 205

Gly Gln Met Ile Trp Gly Ala Thr Leu Asp Glu Ser Ala Ala Asn Pro
    210                 215                 220

Ser Tyr Ser Glu Trp Ala Ala Lys Ala Thr Ala Thr Val Thr Gly Asp
225                 230                 235                 240

Cys Gly Gly Ala Thr Pro Thr Thr Thr Thr Thr Thr Thr Ser Val
                245                 250                 255

Pro Thr Ala Thr Gly Ile Pro Val Pro Thr Gly Thr Tyr Asp Tyr Ile
            260                 265                 270
```

```
Val Val Gly Ala Gly Ala Gly Ile Pro Leu Ala Asp Lys Leu Ser
            275                 280                 285

Glu Ala Gly Lys Ser Val Leu Leu Ile Glu Lys Gly Pro Pro Ser Ser
    290                 295                 300

Gly Arg Trp Gly Gly Thr Leu Lys Pro Glu Trp Leu Lys Asp Thr Asn
305                 310                 315                 320

Leu Thr Arg Phe Asp Val Pro Gly Leu Cys Asn Glu Ile Trp Val Asn
                325                 330                 335

Ser Ala Gly Val Ala Cys Thr Asp Thr Asp Gln Met Ala Gly Cys Val
                340                 345                 350

Leu Gly Gly Gly Thr Ala Val Asn Ala Gly Leu Trp Trp Lys Pro Tyr
            355                 360                 365

Asn Leu Asp Trp Asp Tyr Asn Phe Pro Arg Gly Trp Lys Ser Arg Asp
370                 375                 380

Met Ala Ala Ala Thr Arg Arg Val Phe Ser Arg Ile Pro Gly Thr Asp
385                 390                 395                 400

Asn Pro Ser Met Asp Gly Lys Arg Tyr Leu Gln Gln Gly Phe Glu Ile
                405                 410                 415

Leu Ala Gly Gly Leu Lys Ala Ala Gly Trp Thr Glu Val Thr Ala Asn
            420                 425                 430

Asp Ala Pro Asn Lys Lys Asn His Thr Tyr Ser His Ser Pro Phe Met
                435                 440                 445

Phe Ser Gly Gly Glu Arg Gly Gly Pro Met Gly Thr Tyr Leu Val Ser
    450                 455                 460

Ala Ser Arg Arg Lys Asn Phe His Leu Trp Thr Gly Thr Ala Val Lys
465                 470                 475                 480

Arg Val Val Arg Thr Gly Gly His Ile Thr Gly Leu Glu Val Glu Pro
                485                 490                 495

Phe Val Asn Gly Gly Tyr Thr Gly Val Val Asn Val Thr Ser Ile Thr
            500                 505                 510

Gly Arg Val Val Leu Ser Ala Gly Ala Phe Gly Ser Ala Lys Ile Leu
        515                 520                 525

Leu Arg Ser Gly Ile Gly Pro Glu Asp Gln Leu Glu Ile Val Lys Ser
    530                 535                 540

Ser Thr Asp Gly Pro Thr Met Ile Ser Asp Ser Ser Trp Ile Thr Leu
545                 550                 555                 560

Pro Val Gly Tyr Asn Leu Glu Asp His Thr Asn Thr Asp Thr Val Val
                565                 570                 575

Thr His Pro Asp Val Val Phe Tyr Asp Phe Tyr Glu Ala Gly His Pro
                580                 585                 590

Asn Val Thr Asp Lys Asp Leu Tyr Leu Asn Ser Arg Ala Gly Ile Leu
            595                 600                 605

Ala Gln Ala Ala Pro Asn Ile Gly Pro Met Phe Trp Glu Glu Ile Lys
    610                 615                 620

Gly Lys Asp Gly Val Val Arg Gln Leu Gln Trp Thr Ala Arg Val Glu
625                 630                 635                 640

Gly Ser Ala Gly Thr Pro Asn Gly Tyr Ala Met Thr Met Ser Gln Tyr
                645                 650                 655

Leu Gly Arg Gly Ala Lys Ser Arg Gly Arg Met Thr Ile Thr Lys Ala
            660                 665                 670

Leu Thr Thr Val Val Ser Thr Val Pro Tyr Leu Gln Asp Lys Asn Asp
        675                 680                 685
```

```
Val Glu Ala Val Ile Gln Gly Ile Lys Asn Leu Gln Ala Ala Leu Ser
    690                 695                 700

Asn Val Lys Asn Leu Thr Trp Thr Tyr Pro Pro Ser Asn Thr Thr Val
705                 710                 715                 720

Glu Asp Phe Val Asn Asn Met Leu Val Ser Tyr Thr Asn Arg Arg Ser
                725                 730                 735

Asn His Trp Ile Gly Thr Asn Lys Leu Gly Thr Asp Asp Gly Arg Ser
            740                 745                 750

Arg Gly Gly Ser Ala Val Val Asp Leu Asn Thr Lys Val Tyr Gly Thr
        755                 760                 765

Asp Asn Leu Phe Val Val Asp Ala Gly Ile Phe Pro Gly His Ile Thr
    770                 775                 780

Thr Asn Pro Thr Ser Tyr Ile Val Ile Ala Ala Glu Arg Ala Ser Glu
785                 790                 795                 800

Arg Ile Leu Asp Leu Pro Pro Ala Arg Ala Gln Pro Arg Phe Ala Gln
                805                 810                 815

Cys Gly Gly Arg Thr Trp Thr Gly Ser Phe Gln Cys Ala Ala Pro Tyr
            820                 825                 830

Thr Cys Gln Tyr Arg Asn Glu Arg Tyr Ser Gln Cys Arg
        835                 840                 845

<210> SEQ ID NO 4
<211> LENGTH: 2520
<212> TYPE: DNA
<213> ORGANISM: Hypoxylon haematostroma

<400> SEQUENCE: 4
atgggtcgcc taggctctct cgcgaagttg cttctcgcag tcggcttgaa tgttcagcaa      60
tgcttcgggc aaaacggacc cccgaccccc tacactgata gtgagaccgg tatcactttc     120
gccacctggt ccggcggaaa cggcttagca ccctggggcg gcttgacttt cggtgttgcg     180
ttacctgaaa atgccctgac caccgacgct accgagctga ttggataccct gaaatgcggt     240 tccaatggca aaccacaga tgcgtggtgt ggtctgtcgt ttggggggccc gatgactaac     300 agcctccttc tcatggcctg gccgcacgaa gacgagatct tgacatcatt ccgttttgcc     360
agtggatata ccagaccaga cctatacacc ggcgatgcca aattaacgca gatatcatcc     420
accatcgata aagatcactt tactctaatt ttcaggtgcc agaactgtct agcgtggaac     480
caagacggcg cgtctggttc cgcttcaact agtgccggct ccttgatatt aggctgggcc     540
agtgcgcttc gggcccccgac gaatgcaggc tgtccggctg aaatcaactt caacttccac     600
aacaatggcc agatgatatg gggcgctaca ttagacgaga gcgccgcaaa cccatcatat     660
tcggaatggg ctgccaaagc caccgctacg gttaccggtg actgcggcgg tgcaaccccct     720 acgaccacta ctaccaccac cacgtccgtc cctaccgcca caggtatccc agtgccaact     780
ggcacctacg actatattgt agttggtgcg ggtgctggcg aataccttt ggccgacaag     840 ctgagcgagg ctggaaagag tgtgttactg atcgaaaagg ggccgccatc atcgggacga     900
tggggtggca ccctcaagcc agagtggttg aaggacacca acttgacacg gtttgacgtc     960
cctggcctgt gcaatcagat ctgggtcaac tctgcaggcg tcgcttgtac tgacacagac     1020
caaatggccg gttgcgttct tggtggtggt acagctgtca acgctggcct atggtggaag     1080
ccctacaacc tcgactggga ttataacttc ccacgcggat ggaagtccag ggatatggcc     1140
gctgcaacca ggagagtctt ctctcgcatt cccgtacaa taatccctc aatggatggc     1200 aagcggtatt tacagcaagg cttcgaaatc ctcgctggtg gcttgaaagc cgctggatgg     1260
```

```
accgaggtta ccgcgaatga cgcacccaat aagaagaacc acacctactc acactcgccg    1320
ttcatgttct ccggcggcga acggggtggc ccaatgggca cctacctggt atcggccagt    1380
agacgtaaga atttccatct atggacggga acagcagtga agagggttgt tcgcacaggc    1440
ggccatatca ccggtctgga ggtcgagccc ttcgtaaacg gcggttatac cggtgttgtc    1500
aacgtcacct cgattactgg tcgggtcgtc ttgtctgctg gtgcgttcgg gtcggctaag    1560
atattactga ggagcggcat cggacctgag gatcagttgg agattgtcaa gtcatcaacc    1620
gatggcccga ccatgatttc cgattcttct tggattacgc tacccgtcgg ttataatcta    1680
gaggatcaca caaacaccga cacggtcgtt acgcatcctg acgtcgtatt ttacgacttc    1740
tacgaggctg acatcctaa tgttaccgac aaggacttgt atctcaactc acgggccgga    1800
atccttgctc aagcagcgcc taatatcggc ccaatgttct gggaagagat taagggtagg    1860
gacggcgtcg ttagacagct ccagtggaca gccagagttg aaggaagtgc cggtacaccg    1920
aatgggtacg ccatgacaat gagccaatac cttggacgag cgctaagtc gaggggccga    1980 atgactatca cgaaggcgtt gacgaccgtc gtttctacag taccttacct acaggataag    2040
aacgacgtgg aagcagtcat ccagggaatc aagaaccttc aagcagcact ttcgaacgtg    2100
aagaatctca catgggccta cccaccatct aatacgacgg tggaggactt tgttaacaac    2160
atgctggttt catacactaa taggcgttcc aaccactgga ttgggaccaa caagctcgga    2220
accgatgatg gccgatcgcg cggaggttca gctgtcgtgg acctcaacac taaggtatac    2280
ggcaccgaca acctgttcgt cgttgacgca ggaatattcc ccggtcatat taccacgaac    2340
ccgacttcgt atatcgtgat cgccgctgag cgcgcttctg agaggatcct cgaccttccc    2400
ccggctagag cacaaccgcg cttcgcgcag tgcggcgggc gaacgtggac gggtagcttc    2460
cagtgtgcag cgccgtacac ttgtcagtac aggaatgagc ggtattccca gtgccggtaa    2520

<210> SEQ ID NO 5
<211> LENGTH: 831
<212> TYPE: PRT
<213> ORGANISM: Chaetomium atrobrunneum

<400> SEQUENCE: 5

Met Arg Pro Ser Ser Arg Phe Val Gly Ala Leu Ala Ala Ala Ser
1               5                   10                  15

Phe Leu Pro Ser Ala Leu Ala Gln Asn Asn Ala Ala Val Thr Phe Thr
                20                  25                  30

Asp Pro Asp Thr Gly Ile Val Phe Asn Ser Trp Gly Leu Ala Asn Gly
            35                  40                  45

Ala Pro Gln Thr Gln Gly Gly Phe Thr Phe Gly Val Ala Leu Pro Ser
        50                  55                  60

Asp Ala Leu Thr Thr Asp Ala Thr Glu Phe Ile Gly Tyr Leu Glu Cys
65                  70                  75                  80

Ala Ser Ala Asp Asn Gln Gly Trp Cys Gly Val Ser Met Gly Gly Pro
                85                  90                  95

Met Thr Asn Ser Leu Leu Ile Thr Ala Trp Pro His Glu Asp Asn Val
                100                 105                 110

Tyr Thr Ser Leu Arg Phe Ala Thr Gly Tyr Ala Met Pro Asp Val Tyr
            115                 120                 125

Ser Gly Asp Ala Thr Ile Thr Gln Ile Ser Ser Ile Asn Ala Thr
        130                 135                 140

His Phe Lys Leu Ile Phe Arg Cys Gln Asn Cys Leu Gln Trp Thr His
```

-continued

```
            145                 150                 155                 160
        Asp Gly Ala Ser Gly Ala Ser Thr Ser Ala Gly Val Leu Val Leu
                        165                 170                 175
        Gly Trp Val Gln Ala Phe Pro Ser Pro Gly Asn Pro Thr Cys Pro Asp
                        180                 185                 190
        Gln Ile Thr Leu Glu Gln His Asn Asn Gly Met Gly Ile Trp Gly Ala
                        195                 200                 205
        Val Met Asp Ser Asn Val Ala Asn Pro Ser Tyr Thr Glu Trp Ala Ala
                        210                 215                 220
        Gln Ala Thr Lys Thr Val Glu Ala Glu Cys Asp Gly Pro Ser Glu Thr
        225                 230                 235                 240
        Asp Ile Val Gly Val Pro Val Pro Thr Gly Thr Thr Phe Asp Tyr Ile
                        245                 250                 255
        Val Val Gly Gly Gly Ala Gly Gly Ile Pro Thr Ala Asp Lys Leu Ser
                        260                 265                 270
        Glu Ala Gly Lys Ser Val Leu Leu Ile Glu Lys Gly Ile Ala Ser Thr
                        275                 280                 285
        Ala Glu His Gly Gly Thr Leu Gly Pro Glu Trp Leu Glu Gly Asn Asp
                        290                 295                 300
        Leu Thr Arg Phe Asp Val Pro Gly Leu Cys Asn Gln Ile Trp Val Asp
        305                 310                 315                 320
        Ser Lys Gly Ile Ala Cys Glu Asp Thr Asp Gln Met Ala Gly Cys Val
                        325                 330                 335
        Leu Gly Gly Gly Thr Ala Val Asn Ala Gly Leu Trp Phe Lys Pro Tyr
                        340                 345                 350
        Ser Leu Asp Trp Asp Tyr Leu Phe Pro Ser Gly Trp Lys Tyr Arg Asp
                        355                 360                 365
        Ile Gln Ala Ala Ile Gly Arg Val Phe Ser Arg Ile Pro Gly Thr Asp
                        370                 375                 380
        Ala Pro Ser Thr Asp Gly Lys Arg Tyr Gln Gln Gly Phe Asp Val
        385                 390                 395                 400
        Leu Ala Gly Gly Leu Ser Ala Gly Gly Trp Asn Lys Val Thr Ala Asn
                        405                 410                 415
        Ser Ser Pro Asp Lys Lys Asn Arg Thr Phe Ser Asn Ala Pro Phe Met
                        420                 425                 430
        Phe Ser Gly Gly Glu Arg Gly Gly Pro Leu Ala Thr Tyr Leu Thr Ser
                        435                 440                 445
        Ala Lys Lys Arg Ser Asn Phe Asn Leu Trp Leu Asn Thr Ser Val Lys
                        450                 455                 460
        Arg Val Ile Arg Glu Gly Gly His Val Thr Gly Val Glu Val Glu Pro
        465                 470                 475                 480
        Phe Arg Thr Gly Gly Tyr Gln Gly Ile Val Asn Val Thr Ala Val Ser
                        485                 490                 495
        Gly Arg Val Val Leu Ser Ala Gly Thr Phe Gly Ser Ala Lys Ile Leu
                        500                 505                 510
        Leu Arg Gly Gly Ile Gly Pro Ala Asp Gln Leu Glu Val Val Lys Ala
                        515                 520                 525
        Ser Lys Ile Asp Gly Pro Thr Met Ile Ser Asn Ala Ser Trp Ile Pro
                        530                 535                 540
        Leu Pro Val Gly Tyr Asn Leu Asp Asp His Leu Asn Thr Asp Thr Val
        545                 550                 555                 560
        Ile Thr His Pro Asp Val Ala Phe Tyr Asp Phe Tyr Glu Ala Trp Asn
                        565                 570                 575
```

```
Thr Pro Ile Glu Ala Asp Lys Asn Ser Tyr Leu Ser Ser Arg Thr Gly
            580                 585                 590

Ile Leu Ala Gln Ala Ala Pro Asn Ile Gly Pro Met Met Trp Glu Glu
        595                 600                 605

Ile Lys Gly Ala Asp Gly Ile Val Arg Gln Leu Gln Trp Thr Ala Arg
    610                 615                 620

Val Glu Gly Ser Phe Asp Thr Pro Asn Gly Gln Ala Met Thr Ile Ser
625                 630                 635                 640

Gln Tyr Leu Gly Arg Gly Ala Thr Ser Arg Gly Arg Met Thr Ile Thr
                645                 650                 655

Pro Ser Leu Thr Thr Val Val Ser Asp Val Pro Tyr Leu Lys Asp Pro
            660                 665                 670

Asn Asp Lys Glu Ala Val Ile Gln Gly Ile Val Asn Leu Gln Asn Ala
        675                 680                 685

Leu Lys Asn Val Ala Gly Leu Thr Trp Thr Tyr Pro Asn Ser Ser Ile
    690                 695                 700

Thr Pro Arg Glu Tyr Val Asp Asn Met Val Val Ser Pro Ser Asn Arg
705                 710                 715                 720

Arg Ala Asn His Trp Met Gly Thr Ala Lys Ile Gly Thr Asp Asp Gly
                725                 730                 735

Arg Leu Ala Gly Gly Ser Ala Val Val Asp Leu Asn Thr Lys Val Tyr
            740                 745                 750

Gly Thr Asp Asn Leu Phe Val Val Asp Ala Ser Ile Phe Pro Gly Thr
        755                 760                 765

Pro Thr Thr Asn Pro Ser Ala Tyr Ile Val Thr Ala Ala Glu His Ala
    770                 775                 780

Ser Gln Arg Ile Leu Gly Leu Ala Ala Pro Lys Pro Val Gly Lys Trp
785                 790                 795                 800

Gly Gln Cys Gly Gly Arg Gln Trp Thr Gly Ser Phe Gln Cys Val Ser
                805                 810                 815

Gly Thr Lys Cys Glu Val Val Asn Glu Trp Tyr Ser Gln Cys Leu
            820                 825                 830

<210> SEQ ID NO 6
<211> LENGTH: 2496
<212> TYPE: DNA
<213> ORGANISM: Chaetomium atrobrunneum

<400> SEQUENCE: 6
atgaggccct cctctcggtt tgttggtgcc ctggcggcgg cggcgtcgtt cctgccgtct      60
gcccttgccc agaacaatgc tgcagtcacc ttcactgacc cggacaccgg catcgtcttc     120
aactcctggg gtcttgccaa tggagcacca cagactcagg gaggcttcac ctttggtgtc     180
gctctgccct ctgatgcgct cacgaccgat gctaccgagt tcattggtta tttggaatgt     240
gcctccgcgg acaaccaggg ctggtgcggt gtctcgatgg gcggcccat gaccaactcg      300 cttcttatca ccgcctggcc gcacgaggac aacgtctaca cctccctccg gtttgcaaca     360
ggatacgcca tgccggatgt ctactcggga gacgccacca tcacgcagat ctcgtcgagc     420
atcaacgcga cccacttcaa gctcatcttc aggtgccaga actgcctgca atggacccac     480
gacggcgctt ccggtggcgc ctccacgtct gccggtgttc tggtcctcgg ctgggtccag     540
gctttccctt ccctggcaa cccgacgtgc ccggaccaga tcacgctcga gcagcacaac     600
aacggcatgg gcatctgggg tgcggtgatg gactccaacg tcgccaaccc gtcctacaca     660
```

```
gagtgggccg cgcaggccac caagacggtc gaggccgagt gcgacggccc gagtgagacg    720
gatattgtcg gcgtgcccgt gccgaccggc accaccttcg actacatcgt cgtgggcggc    780
ggtgccggcg gtatccccac tgccgacaag ctcagcgagg ccggcaagag tgtgctgctg    840
attgagaagg gcatcgcctc gactgctgag cacggcggca ctctcggacc cgagtggctc    900
gagggcaacg acctgacgcg gttcgacgtg cccggtcttt gcaaccagat ctgggttgac    960
tccaagggca tcgcctgcga ggacaccgac cagatggccg gttgcgtcct cggcggcggc   1020
acggccgtca acgccggcct ctggttcaag ccctactcgc tcgactggga ctacctcttc   1080
ccaagcggct ggaagtaccg cgacatccag gccgccatcg cagggtgtt ctcgcgcatc    1140
ccgggcactg acgcgccctc gaccgacggc aagcgctact accagcaggg cttcgacgtg   1200
ctcgcgggcg gcctgagtgc cggcggctgg aacaaggtca cggccaactc gtctccagac   1260
aagaagaacc gcaccttctc gaacgcgcct ttcatgttct cgggcggcga gcgcggcggg   1320
cccctggcca cttatctcac cagcgccaag aagcgcagca acttcaacct gtggctcaac   1380
acgtcggtca agcgcgtcat ccgtgagggc ggccacgtca caggtgtcga ggtcgagcct   1440
ttccggacgg gcgggtacca gggtatcgtg aacgttaccg ccgtttcggg ccgtgtcgtc   1500
ctgtcggctg gtaccttcgg cagtgccaag attctgctca gaggcggtat tggcccagcg   1560
gatcagctcg aggttgtcaa ggcgtcgaag atcgacgggc cgaccatgat cagcaatgcg   1620
tcttggattc ctctgcctgt tgggtacaac ctggatgacc atctcaacac tgacactgtc   1680
attacccacc ccgacgttgc cttctacgac ttctacgagg catggaacac gcccattgag   1740
gcggacaaga cagctacct gagcagccgc actggtatcc tcgctcaggc cgcgcccaac    1800
attggcccaa tgatgtggga ggaaatcaag ggtgccgacg gtatcgtccg ccagctgcaa   1860
tggaccgccc gtgtcgaggg tagctttgac acgcctaacg gcaggcgat gaccatctcg    1920
cagtacctcg ccgcggcgc gacctcgcgc ggccgtatga ccatcacccc ttcgctgacg   1980
accgtcgtct cggacgtgcc gtacctcaag gacccgaacg ataaggaggc cgtcatccag   2040
ggcatcgtca acctgcagaa cgccctcaaa acgtcgccg gcctgacctg gacctacccc    2100
aactcgagca tcacaccgcg cgaatacgtc gataatatgg tagtctcccc tagcaaccgg   2160
cgcgcaaacc actggatggg cacggccaaa atcggcaccg acgacggccg cctggccggc   2220
ggctccgccg tcgtggactt gaacaccaag gtctacggca ccgacaacct ctttgtcgtg   2280
gacgcgtcca tcttccccgg cacgcccacc accaatccct cggcgtacat cgtcacggct   2340
gcggagcatg cttcgcagag gatcttgggg ttggctgcgc cgaagccggt tgggaaatgg   2400
ggccagtgtg gcgggcggca gtggacaggg agcttccagt gcgtgagtgg acaaagtgt    2460
gaggtggtga atgagtggta ctcgcagtgc ttgtag                              2496
```

<210> SEQ ID NO 7
<211> LENGTH: 787
<212> TYPE: PRT
<213> ORGANISM: Corynascus thermophilus

<400> SEQUENCE: 7

Met Lys Leu Leu Ser Arg Val Gly Ala Thr Ala Leu Ala Ala Thr Leu
1               5                   10                  15

Ser Leu Lys Gln Cys Ala Ala Gln Met Thr Glu Gly Thr Tyr Thr His
            20                  25                  30

Glu Ala Thr Gly Ile Thr Phe Lys Thr Trp Thr Pro Ser Asp Gly Ser
        35                  40                  45

-continued

```
Thr Phe Thr Phe Gly Leu Ala Leu Pro Gly Asp Ala Leu Thr Asn Asp
    50                  55                  60

Ala Thr Glu Tyr Ile Gly Leu Leu Arg Cys Gln Ile Thr Asp Pro Ser
 65                  70                  75                  80

Ser Pro Gly Tyr Cys Gly Ile Ser His Gly Gln Ser Gly Gln Met Thr
                 85                  90                  95

Gln Ala Leu Leu Leu Val Ala Trp Ala Ser Glu Asp Val Val Tyr Thr
                100                 105                 110

Ser Phe Arg Tyr Ala Thr Gly Tyr Thr Leu Pro Glu Leu Tyr Thr Gly
            115                 120                 125

Asp Ala Lys Leu Thr Gln Ile Ala Ser Ser Val Ser Gly Asp Ser Phe
130                 135                 140

Glu Val Leu Phe Arg Cys Glu Asn Cys Phe Ser Trp Asp Gln Asn Gly
145                 150                 155                 160

Ala Thr Gly Ser Val Ser Thr Ser Asn Gly Ala Leu Val Leu Gly Tyr
                165                 170                 175

Ala Ala Ser Lys Ser Gly Leu Thr Gly Ala Thr Cys Pro Asp Thr Ala
            180                 185                 190

Glu Phe Gly Phe His Asn Asn Gly Phe Gly Gln Trp Gly Ala Val Leu
        195                 200                 205

Glu Gly Ala Thr Ser Asp Ser Tyr Glu Glu Trp Ala Gln Leu Ala Thr
    210                 215                 220

Ile Thr Pro Pro Thr Thr Cys Asp Gly Asn Gly Pro Gly Asp Lys Val
225                 230                 235                 240

Cys Val Pro Ala Pro Glu Asp Thr Tyr Asp Tyr Ile Val Val Gly Ala
                245                 250                 255

Gly Ala Gly Gly Ile Thr Val Ala Asp Lys Leu Ser Glu Ala Gly His
            260                 265                 270

Lys Val Leu Leu Ile Glu Lys Gly Pro Pro Ser Thr Gly Leu Trp Asn
        275                 280                 285

Gly Thr Met Lys Pro Glu Trp Leu Glu Gly Thr Asp Leu Thr Arg Phe
    290                 295                 300

Asp Val Pro Gly Leu Cys Asn Gln Ile Trp Val Asp Ser Ala Gly Ile
305                 310                 315                 320

Ala Cys Thr Asp Thr Asp Gln Met Ala Gly Cys Val Leu Gly Gly Gly
                325                 330                 335

Thr Ala Val Asn Ala Gly Leu Trp Trp Lys Pro His Pro Ala Asp Trp
            340                 345                 350

Asp Asp Asn Phe Pro His Gly Trp Lys Ser Ser Asp Leu Ala Asp Ala
        355                 360                 365

Thr Glu Arg Val Phe Ser Arg Ile Pro Gly Thr Trp His Pro Ser Gln
    370                 375                 380

Asp Gly Lys Leu Tyr Arg Gln Glu Gly Phe Glu Val Ile Ser Gln Gly
385                 390                 395                 400

Leu Ala Asn Ala Gly Trp Arg Glu Val Asp Ala Asn Gln Glu Pro Ser
                405                 410                 415

Glu Lys Asn Arg Thr Tyr Ser His Ser Val Phe Met Phe Ser Gly Gly
            420                 425                 430

Glu Arg Gly Gly Pro Leu Ala Thr Tyr Leu Ala Ser Ala Ala Gln Arg
        435                 440                 445

Ser Asn Phe Asn Leu Trp Val Asn Thr Ser Val Arg Arg Ala Ile Arg
    450                 455                 460

Thr Gly Pro Arg Val Ser Gly Val Glu Leu Glu Cys Leu Ala Asp Gly
```

```
            465                 470                 475                 480
        Gly Phe Asn Gly Thr Val Asn Leu Lys Glu Gly Gly Val Ile Phe
                        485                 490                 495
        Ser Ala Gly Ala Phe Gly Ser Ala Lys Leu Leu Arg Ser Gly Ile
                        500                 505                 510
        Gly Pro Glu Asp Gln Leu Glu Ile Val Ala Ser Ser Lys Asp Gly Glu
                        515                 520                 525
        Thr Phe Ile Ser Lys Asn Asp Trp Ile Lys Leu Pro Val Gly His Asn
                        530                 535                 540
        Leu Ile Asp His Leu Asn Thr Asp Leu Ile Ile Thr His Pro Asp Val
        545                 550                 555                 560
        Val Phe Tyr Asp Phe Tyr Ala Ala Trp Asp Asn Pro Ile Thr Glu Asp
                        565                 570                 575
        Lys Glu Ala Tyr Leu Asn Ser Arg Ser Gly Ile Leu Ala Gln Ala Ala
                        580                 585                 590
        Pro Asn Ile Gly Pro Leu Met Trp Glu Glu Val Thr Pro Ser Asp Gly
                        595                 600                 605
        Ile Thr Arg Gln Phe Gln Trp Thr Cys Arg Val Glu Gly Asp Ser Ser
                        610                 615                 620
        Lys Thr Asn Ser Thr His Ala Met Thr Leu Ser Gln Tyr Leu Gly Arg
        625                 630                 635                 640
        Gly Val Val Ser Arg Gly Arg Met Gly Ile Thr Ser Gly Leu Thr Thr
                        645                 650                 655
        Thr Val Ala Glu His Pro Tyr Leu His Asn Asp Gly Asp Leu Glu Ala
                        660                 665                 670
        Val Ile Gln Gly Ile Gln Asn Val Val Asp Ala Leu Ser Gln Val Pro
                        675                 680                 685
        Asp Leu Glu Trp Val Leu Pro Pro Asn Thr Thr Val Glu Glu Tyr
                        690                 695                 700
        Val Asn Ser Leu Ile Val Ser Pro Ala Asn Arg Arg Ala Asn His Trp
        705                 710                 715                 720
        Met Gly Thr Ala Lys Met Gly Leu Asp Asp Gly Arg Ser Gly Gly Ser
                        725                 730                 735
        Ala Val Val Asp Leu Asn Thr Lys Val Tyr Gly Thr Asp Asn Leu Phe
                        740                 745                 750
        Val Val Asp Ala Ser Ile Phe Pro Gly Met Ser Thr Gly Asn Pro Ser
                        755                 760                 765
        Ala Met Ile Val Ile Val Ala Glu Gln Ala Ala Gln Arg Ile Leu Ser
        770                 775                 780
        Leu Arg Tyr
        785

<210> SEQ ID NO 8
<211> LENGTH: 2364
<212> TYPE: DNA
<213> ORGANISM: Corynascus thermophilus

<400> SEQUENCE: 8
atgaagcttc tcagccgcgt tgggccacc gccctagcgg cgacgttgtc cctgaaacaa      60
tgtgcagctc agatgaccga agggacgtac acccatgagg ctaccggtat cacgttcaag     120
acatggactc cttccgacgg ctcgacttc acttcggct tggccctccc tggggacgcg       180
ctgacaaatg atgccaccga gtacattggt ctcctgcgtt gccaaatcac cgatccctct     240
tcgcccggct actgtggcat ctcccacggc cagtccggcc agatgacgca ggcgctgctg     300
```

```
ctggtcgctt gggccagcga ggatgtcgtc tacacgtcgt tccgctacgc caccggctac    360
acactccccg agctctacac gggcgacgcc aagctgaccc agatcgcctc ctcggtcagc    420
ggggacagct tcgaggtgct gttccgctgc gagaactgct tctcctggga ccagaacggc    480
gccacgggca gtgtctcgac cagcaacggc gccctggttc tcggctacgc tgcctcgaag    540
agtggtttga cgggcgccac gtgcccggac acggccgagt ttggcttcca caacaatggt    600
ttcggacagt ggggtgcagt gctcgagggt gcgacctcgg actcgtatga ggagtgggct    660
cagctggcca ctatcacgcc cccgaccacc tgcgatggca acggccctgg cgacaaggtg    720
tgcgttccgg ctcccgaaga cacgtatgat tacatcgttg tcggcgccgg cgccggcggc    780
atcacggtcg ccgacaagct cagcgaggcc ggccacaagg tcctccttat cgagaagggt    840
cctccgtcga ccggcctgtg aacgggacc atgaagcccg agtggctcga gggtaccgac    900
ctcacccgct cgacgtccc cggtctgtgc aaccagatct gggtcgactc tgccggcatt    960
gcctgcaccg ataccgacca gatggcgggc tgcgttctcg gcgtggcac cgctgtcaat   1020 gctggtctgt ggtggaagcc ccaccccgct gactgggacg acaacttccc tcatggctgg   1080
aagtcgagcg atctcgcgga tgcgaccgag cgtgtcttca gccgcattcc cggcacgtgg   1140
cacccgtcgc aggatggcaa actgtaccgc caggagggct cgaggtcat cagccagggc   1200 ctggccaacg ccggctggag ggaagtcgac gccaaccagg agcccagcga agaaccgc    1260 acgtattccc acagtgtgtt catgttctcg ggcggtgagc gcggcggccc cctggcgacg   1320
tacctcgcct cggctgccca gcgcagcaac ttcaacttgt gggtcaacac ttcggtccgg   1380
agggccatcc gcaccggccc cagggtcagt ggcgtcgaac tcgagtgcct tgcggacggc   1440
ggcttcaacg gtactgtcaa cctgaaggag ggtggtggtg tcatcttttc ggctggcgct   1500
ttcggctcgg ccaagctgct ccttcgcagc ggcatcggtc ctgaggacca gctcgagatt   1560
gtggcgagct ccaaggacgg cgagaccttc atttccaaga atgattggat caagctcccc   1620
gtcggccata acctgatcga tcatctcaac accgacctca ttattactca cccggatgtc   1680
gttttctatg acttctacgc ggcttgggac aatcccatca ccgaggacaa ggaggcctac   1740
ctgaactcgc ggtccggcat tctcgcccaa gcggcgccca acatcggccc tctgatgtgg   1800
gaggaagtca cgccatccga cggcatcacc cgccagttcc agtggacatg ccgtgttgag   1860
ggcgacagct ccaagaccaa ctcgacccac gccatgaccc tcagccagta tctcggccgt   1920
ggcgtcgtct cgcgcggccg gatgggcatc acttccgggc tgaccacgac ggtggccgag   1980
cacccgtacc tgcacaacga cggcgacctg gaggcggtga tccagggtat ccagaacgtg   2040
gtggacgcgc tcagccaggt gcccgacctc gagtgggtgc tcccgccgcc caacacgacg   2100
gtggaggaat acgtcaacag cctgatcgtg tctccggcta accgccgggc caaccactgg   2160
atgggcacgg ccaagatggg cctcgatgac ggccgctcgg cggctccgc ggtcgtcgac   2220 ctcaacacaa aggtgtatgg caccgacaac ctgtttgtcg tcgacgcctc catcttccct   2280
ggcatgtcga cgggcaaccc gtcggctatg atcgtcatcg tggccgagca ggcggcccag   2340
cgcatcctgt ccctgcggta ttag                                         2364
```

<210> SEQ ID NO 9
<211> LENGTH: 829
<212> TYPE: PRT
<213> ORGANISM: Stachybotris bisb -continued

```
Met Leu Phe Lys Leu Ser Asn Trp Leu Leu Ala Leu Ala Leu Phe Val
 1               5                  10                  15

Gly Asn Val Val Ala Gln Leu Val Gly Pro Thr Pro Tyr Thr Asp Pro
             20                  25                  30

Asp Thr Gly Ile Val Phe Gln Ser Trp Val Asn Pro Ala Gly Thr Leu
             35                  40                  45

Lys Phe Gly Tyr Thr Tyr Pro Ala Asn Ala Ala Thr Val Ala Ala Thr
 50                  55                  60

Glu Phe Ile Gly Phe Leu Glu Cys Gln Gly Ala Gly Trp Cys Ser Val
 65                  70                  75                  80

Ser Leu Gly Gly Ser Met Leu Asn Lys Pro Leu Val Val Ala Tyr Pro
                 85                  90                  95

Ser Gly Asp Glu Val Leu Ala Ser Leu Lys Trp Ala Thr Gly Tyr Ala
             100                 105                 110

Asn Pro Glu Pro Tyr Gly Gly Asn His Lys Leu Ser Gln Ile Ser Ser
             115                 120                 125

Ser Val Thr Ser Ala Gly Phe Arg Val Val Tyr Arg Cys Glu Gly Cys
             130                 135                 140

Leu Ala Trp Asn Tyr Gln Gly Ile Glu Gly Gly Ser Pro Thr Asn Gly
145                 150                 155                 160

Ala Ser Met Pro Ile Gly Trp Ala Tyr Ser Ala Ser Ser Val Leu Asn
             165                 170                 175

Gly Asp Cys Val Asp Asn Thr Val Leu Ile Gln His Asp Thr Phe Gly
             180                 185                 190

Asn Tyr Gly Phe Val Pro Asp Glu Ser Ser Leu Arg Thr Glu Tyr Asn
             195                 200                 205

Asp Trp Thr Glu Leu Pro Thr Arg Val Val Arg Gly Asp Cys Gly Gly
             210                 215                 220

Ser Thr Thr Thr Ser Ser Val Pro Ser Ser Thr Ala Pro Pro Gln Gly
225                 230                 235                 240

Thr Gly Ile Pro Val Pro Thr Gly Ala Ser Tyr Asp Tyr Ile Val Val
             245                 250                 255

Gly Ser Gly Ala Gly Gly Ile Pro Ile Ala Asp Lys Leu Thr Glu Ala
             260                 265                 270

Gly Lys Lys Val Leu Leu Ile Glu Lys Gly Pro Pro Ser Ser Gly Arg
             275                 280                 285

Tyr Asp Gly Lys Leu Lys Pro Thr Trp Leu Glu Gly Thr Asn Leu Thr
             290                 295                 300

Arg Phe Asp Val Pro Gly Leu Cys Asn Gln Ile Trp Val Asp Ser Ala
305                 310                 315                 320

Gly Ile Ala Cys Arg Asp Thr Asp Gln Met Ala Gly Cys Val Leu Gly
             325                 330                 335

Gly Gly Thr Ala Val Asn Ala Gly Leu Trp Trp Lys Pro Asn Pro Ile
             340                 345                 350

Asp Trp Asp Tyr Asn Phe Pro Ser Gly Trp Lys Ser Ser Glu Met Ile
             355                 360                 365

Gly Ala Thr Asn Arg Val Phe Ser Arg Ile Gly Gly Thr Thr Val Pro
             370                 375                 380

Ser Gln Asp Gly Lys Thr Tyr Tyr Gln Gln Gly Phe Asn Val Leu Ser
385                 390                 395                 400

Ser Gly Leu Lys Ala Ala Gly Trp Thr Ser Val Ser Leu Asn Asn Ala
             405                 410                 415

Pro Ala Gln Lys Asn Arg Thr Tyr Gly Ala Gly Pro Phe Met Phe Ser
```

-continued

```
            420                 425                 430
Gly Gly Glu Arg Gly Gly Pro Leu Ala Thr Tyr Leu Ala Thr Ala Lys
            435                 440                 445
Lys Arg Gly Asn Phe Asp Leu Trp Thr Asn Thr Gln Val Lys Arg Val
450                 455                 460
Ile Arg Gln Gly Gly His Val Thr Gly Val Glu Val Glu Asn Tyr Asn
465                 470                 475                 480
Gly Asp Gly Tyr Lys Gly Thr Val Lys Val Thr Pro Val Ser Gly Arg
                485                 490                 495
Val Val Leu Ser Ala Gly Thr Phe Gly Ser Ala Lys Leu Leu Leu Arg
            500                 505                 510
Ser Gly Ile Gly Pro Lys Asp Gln Leu Ala Ile Val Lys Asn Ser Thr
        515                 520                 525
Asp Gly Pro Thr Met Ala Ser Glu Arg Asp Trp Ile Asn Leu Pro Val
    530                 535                 540
Gly Tyr Asn Leu Glu Asp His Thr Asn Thr Asp Ile Val Ile Ser His
545                 550                 555                 560
Pro Asp Val Val His Tyr Asp Phe Tyr Glu Ala Trp Thr Ala Pro Ile
                565                 570                 575
Glu Ser Asp Lys Thr Ala Tyr Leu Gly Lys Arg Ser Gly Ile Leu Ala
            580                 585                 590
Gln Ala Ala Pro Asn Ile Gly Pro Leu Phe Phe Asp Glu Val Arg Gly
        595                 600                 605
Ala Asp Asn Ile Val Arg Ser Ile Gln Tyr Thr Ala Arg Val Glu Gly
    610                 615                 620
Asn Ser Val Val Pro Asn Gly Lys Ala Met Val Ile Ser Gln Tyr Leu
625                 630                 635                 640
Gly Arg Gly Ala Val Ser Arg Gly Arg Met Thr Ile Ser Gln Gly Leu
                645                 650                 655
Asn Thr Ile Val Ser Thr Ala Pro Tyr Leu Ser Asn Val Asn Asp Leu
            660                 665                 670
Glu Ala Val Ile Lys Ser Leu Glu Asn Ile Ala Asn Ser Leu Thr Ser
        675                 680                 685
Lys Val Lys Asn Leu Lys Ile Glu Trp Pro Ala Ser Gly Thr Ser Ile
    690                 695                 700
Arg Asp His Val Thr Asn Met Pro Leu Asp Pro Ala Thr Arg Arg Ala
705                 710                 715                 720
Asn His Trp Ile Gly Thr Asn Lys Ile Gly Thr Lys Asp Gly Arg Leu
                725                 730                 735
Thr Gly Gly Asp Ser Val Val Asp Leu Asn Thr Lys Val Tyr Gly Thr
            740                 745                 750
Asp Asn Leu Phe Val Val Asp Ala Ser Ile Phe Pro Gly Met Val Thr
        755                 760                 765
Thr Asn Pro Ser Ala Tyr Ile Val Ile Ala Ala Glu His Ala Ala Ser
    770                 775                 780
Lys Ile Leu Ser Leu Pro Thr Ala Lys Ala Ala Lys Tyr Glu Gln
785                 790                 795                 800
Cys Gly Gly Leu Glu Tyr Asn Gly Asn Phe Gln Cys Ala Ser Gly Leu
                805                 810                 815
Thr Cys Thr Trp Leu Asn Asp Tyr Tyr Trp Gln Cys Thr
            820                 825
```

<210> SEQ ID NO 10

<211> LENGTH: 2490
<212> TYPE: DNA
<213> ORGANISM: Stachybotris bisbyi

<400> SEQUENCE: 10

```
atgctgttca agctctcaaa ttggttgcta gcgcttgcgc tctttgttgg caatgtcgtt     60
gctcaactcg tggggcctac cccgtacacg gatccagata ccggcattgt ctttcagtcc    120
tgggtcaatc cagcagggac cctgaagttt ggttacactt accccgcaaa tgctgctacg    180
gttgccgcca cggaatttat cggtttcctg gaatgccaag ggctggatg gtgtagcgtc    240
tcactcggtg gctccatgct taacaagccg cttgttgttg cctaccctag tggcgatgaa    300
gtcctcgctt ctttgaagtg ggccacaggc tacgcgaatc cagagcctta cggcggcaat    360
cacaagctgt cccagatcag ctcgtccgtc acctctgctg gcttcagggt cgtctatcga    420
tgtgagggat gtctcgcctg gaactaccag ggaattgagg gagggagccc caccaatggt    480
gcgtccatgc ctatcggttg ggcttacagc gcaagttctg tactcaacgg ggattgtgtg    540
gataacactg ttctcattca acatgacacc tttggcaatt atggcttcgt acctgatgaa    600
tcatctcttc gcacggagta caatgactgg acggagcttc cgaccagggt tgtcaggga    660
gactgcggcg gttccacaac tacctcttcg gtgccctcct caacggcgcc tcctcaaggt    720
actggcatac cggttcctac tggcgcaagc tatgactaca tagttgttgg ctcgggtgct    780
ggaggtattc ccattgcgga taagcttacc gaggctggca aaaaggtttt gttgattgag    840
aagggaccac cctcttctgg tcgctacgat ggaaagctaa agccgacgtg gcttgaggga    900
actaatctca cccgattcga tgtgcctggc ctctgcaacc aaatatgggt cgactccgct    960
ggcattgcat gccgtgatac cgatcagatg gctggttgtg ttcttggcgg tggtactgct   1020
gtcaatgcag gtctatggtg gaagcctaac cctattgatt gggactataa tttcccttca   1080
ggctggaagt caagcgagat gataggcgcg acaaaccgtg tcttttcacg tattggtggt   1140
actactgttc cttcgcagga cggaaagacc tactatcagc aaggtttcaa cgttctttcc   1200
agcggtctca aggctgcggg ctggacatct gttagcctga ataacgcccc tgcgcaaaag   1260
aaccgcacct atggtgctgg ccctttcatg ttctctggtg gagagcgagg tggaccttta   1320
gccacctacc tggccactgc caagaagaga ggaaacttcg acctctggac gaatacccaa   1380
gttaagcgtg taattcgaca gggaggtcat gttactggag tggaggtcga aaactataac   1440
ggtgatgggt acaagggcac tgtcaaggtg actcctgtat ctgggcgagt tgtcctatct   1500
gctggtacct ttggcagtgc taagcttttg ctccgaagcg gtatcggtcc caaggatcaa   1560
ctagctattg tcaagaactc gactgatggc cctactatgg cttccgagag ggactggatt   1620
aatcttcccg ttggctacaa cttggaggac catactaaca ccgacattgt catctcccat   1680
ccagatgtgg tccattacga cttctatgag gcttggacag cgccaatcga gtctgacaag   1740
actgcttatt tgggcaagcg ttctggcatc ctcgctcaag ccgcccccaa catcgggcct   1800
ctcttctttg acgaagttcg cggtgctgac aacattgtcc gctcaattca gtacactgct   1860
cgtgtggagg gcaacagtgt ggtccctaat ggcaaggcca tggtgatcag ccagtacctt   1920
ggtcgtggcg ctgtttccag gggtcgaatg accatctctc aaggtctcaa tacgattgtt   1980
tccaccgctc catacctctc aaacgtcaat gatctcgagg ccgtcattaa gagccttgag   2040
aacatagcga acagcttgac gtcaaaggtt aaaaacctca agattgaatg gcctgcctct   2100
ggtacatcca ttcgcgatca cgtcacgaat atgcctctcg acccggccac ccgccgagcg   2160
aatcattgga ttggcactaa caagatcgga accaaggatg gtcgactgac aggtggtgat   2220
```

```
tccgtcgttg atttgaacac taaggtctat ggtacagaca atctgtttgt ggtcgatgct    2280 tctatttttcc ctggcatggt tacgaccaac ccctcggcct acattgtaat tgccgctgag    2340
catgctgcat cgaagattct gagcctacct actgctaagg ctgccgcgaa gtacgaacaa    2400
tgtggtggcc ttgaatataa tggtaacttt cagtgtgcgt ctggattaac ctgcacttgg    2460
ttaaacgact actactggca gtgtacttaa                                      2490

<210> SEQ ID NO 11
<211> LENGTH: 829
<212> TYPE: PRT
<213> ORGANISM: Neurospora crassa

<400> SEQUENCE: 11
```

Met Arg Thr Thr Ser Ala Phe Leu Ser Gly Leu Ala Val Ala Ser
1               5                   10                  15

Leu Leu Ser Pro Ala Phe Ala Gln Thr Ala Pro Lys Thr Phe Thr His
            20                  25                  30

Pro Asp Thr Gly Ile Val Phe Asn Thr Trp Ser Ala Ser Asp Ser Gln
        35                  40                  45

Thr Lys Gly Gly Phe Thr Val Gly Met Ala Leu Pro Ser Asn Ala Leu
    50                  55                  60

Thr Thr Asp Ala Thr Glu Phe Ile Gly Tyr Leu Glu Cys Ser Ser Ala
65                  70                  75                  80

Lys Asn Gly Ala Asn Ser Gly Trp Cys Gly Val Ser Leu Arg Gly Ala
                85                  90                  95

Met Thr Asn Asn Leu Leu Ile Thr Ala Trp Pro Ser Asp Gly Glu Val
            100                 105                 110

Tyr Thr Asn Leu Met Phe Ala Thr Gly Tyr Ala Met Pro Lys Asn Tyr
        115                 120                 125

Ala Gly Asp Ala Lys Ile Thr Gln Ile Ala Ser Ser Val Asn Ala Thr
    130                 135                 140

His Phe Thr Leu Val Phe Arg Cys Gln Asn Cys Leu Ser Trp Asp Gln
145                 150                 155                 160

Asp Gly Val Thr Gly Gly Ile Ser Thr Ser Asn Lys Gly Ala Gln Leu
                165                 170                 175

Gly Trp Val Gln Ala Phe Pro Ser Pro Gly Asn Pro Thr Cys Pro Thr
            180                 185                 190

Gln Ile Thr Leu Ser Gln His Asp Asn Gly Met Gly Gln Trp Gly Ala
        195                 200                 205

Ala Phe Asp Ser Asn Ile Ala Asn Pro Ser Tyr Thr Ala Trp Ala Ala
    210                 215                 220

Lys Ala Thr Lys Thr Val Thr Gly Thr Cys Ser Gly Pro Val Thr Thr
225                 230                 235                 240

Ser Ile Ala Ala Thr Pro Val Pro Thr Gly Val Ser Phe Asp Tyr Ile
                245                 250                 255

Val Val Gly Gly Gly Ala Gly Gly Ile Pro Val Ala Asp Lys Leu Ser
            260                 265                 270

Glu Ser Gly Lys Ser Val Leu Leu Ile Glu Lys Gly Phe Ala Ser Thr
        275                 280                 285

Gly Glu His Gly Gly Thr Leu Lys Pro Glu Trp Leu Asn Asn Thr Ser
    290                 295                 300

Leu Thr Arg Phe Asp Val Pro Gly Leu Cys Asn Gln Ile Trp Lys Asp
305                 310                 315                 320

```
Ser Asp Gly Ile Ala Cys Ser Asp Thr Asp Gln Met Ala Gly Cys Val
                325                 330                 335

Leu Gly Gly Gly Thr Ala Ile Asn Ala Gly Leu Trp Tyr Lys Pro Tyr
            340                 345                 350

Thr Lys Asp Trp Asp Tyr Leu Phe Pro Ser Gly Trp Lys Gly Ser Asp
        355                 360                 365

Ile Ala Gly Ala Thr Ser Arg Ala Leu Ser Arg Ile Pro Gly Thr Thr
    370                 375                 380

Thr Pro Ser Gln Asp Gly Lys Arg Tyr Leu Gln Gln Gly Phe Glu Val
385                 390                 395                 400

Leu Ala Asn Gly Leu Lys Ala Ser Gly Trp Lys Glu Val Asp Ser Leu
                405                 410                 415

Lys Asp Ser Glu Gln Lys Asn Arg Thr Phe Ser His Thr Ser Tyr Met
            420                 425                 430

Tyr Ile Asn Gly Glu Arg Gly Gly Pro Leu Ala Thr Tyr Leu Val Ser
        435                 440                 445

Ala Lys Lys Arg Ser Asn Phe Lys Leu Trp Leu Asn Thr Ala Val Lys
    450                 455                 460

Arg Val Ile Arg Glu Gly Gly His Ile Thr Gly Val Glu Val Glu Ala
465                 470                 475                 480

Phe Arg Asn Gly Gly Tyr Ser Gly Ile Ile Pro Val Thr Asn Thr Thr
                485                 490                 495

Gly Arg Val Val Leu Ser Ala Gly Thr Phe Gly Ser Ala Lys Ile Leu
            500                 505                 510

Leu Arg Ser Gly Ile Gly Pro Lys Asp Gln Leu Glu Val Val Lys Ala
        515                 520                 525

Ser Ala Asp Gly Pro Thr Met Val Ser Asn Ser Ser Trp Ile Asp Leu
    530                 535                 540

Pro Val Gly His Asn Leu Val Asp His Thr Asn Thr Asp Thr Val Ile
545                 550                 555                 560

Gln His Asn Asn Val Thr Phe Tyr Asp Phe Tyr Lys Ala Trp Asp Asn
                565                 570                 575

Pro Asn Thr Thr Asp Met Asn Leu Tyr Leu Asn Gly Arg Ser Gly Ile
            580                 585                 590

Phe Ala Gln Ala Ala Pro Asn Ile Gly Pro Leu Phe Trp Glu Glu Ile
        595                 600                 605

Thr Gly Ala Asp Gly Ile Val Arg Gln Leu His Trp Thr Ala Arg Val
    610                 615                 620

Glu Gly Ser Phe Glu Thr Pro Asp Gly Tyr Ala Met Thr Met Ser Gln
625                 630                 635                 640

Tyr Leu Gly Arg Gly Ala Thr Ser Arg Gly Arg Met Thr Leu Ser Pro
                645                 650                 655

Thr Leu Asn Thr Val Ser Asp Leu Pro Tyr Leu Lys Asp Pro Asn
            660                 665                 670

Asp Lys Ala Ala Val Gln Gly Ile Val Asn Leu Gln Lys Ala Leu
        675                 680                 685

Ala Asn Val Lys Gly Leu Thr Trp Ala Tyr Pro Ser Ala Asn Gln Thr
    690                 695                 700

Ala Ala Asp Phe Val Asp Lys Gln Pro Val Thr Tyr Gln Ser Arg Arg
705                 710                 715                 720

Ser Asn His Trp Met Gly Thr Asn Lys Met Gly Thr Asp Asp Gly Arg
                725                 730                 735

Ser Gly Gly Thr Ala Val Val Asp Thr Asn Thr Arg Val Tyr Gly Thr
```

|   |   | 740 |   |   | 745 |   |   |   | 750 |   |   |
|---|---|---|---|---|---|---|---|---|---|---|---|

Asp Asn Leu Tyr Val Val Asp Ala Ser Ile Phe Pro Gly Val Pro Thr
        755                  760              765

Thr Asn Pro Thr Ala Tyr Ile Val Val Ala Ala Glu His Ala Ala Ala
    770                775              780

Lys Ile Leu Ala Gln Pro Ala Asn Glu Ala Val Pro Lys Trp Gly Trp
785                790              795            800

Cys Gly Gly Pro Thr Tyr Thr Gly Ser Gln Thr Cys Gln Ala Pro Tyr
        805                  810              815

Lys Cys Glu Lys Gln Asn Asp Trp Tyr Trp Gln Cys Val
    820                825

<210> SEQ ID NO 12
<211> LENGTH: 2490
<212> TYPE: DNA
<213> ORGANISM: Neurospora crassa

<400> SEQUENCE: 12

```
atgaggacca cctcggcctt tctcagcggc ctggcggcgg tggcttcatt gctgtcgccc      60
gccttcgccc aaaccgctcc caagaccttc actcatcctg ataccggcat tgtcttcaac     120
acatggagtg cttccgattc ccagaccaaa ggtggcttca ctgttggtat ggctctgccg     180
tcaaatgctc ttactaccga cgcgactgaa ttcatcggtt atctggaatg ctcctccgcc     240
aagaatggtg ccaatagcgg ttggtgcggt gtttctctca gaggcgccat gaccaacaat     300
ctactcatta ccgcctggcc ttctgacgga gaagtctaca ccaatctcat gttcgccacg     360
ggttacgcca tgcccaagaa ctacgctggt gacgccaaga tcacccagat cgcgtccagc     420
gtgaacgcta cccacttcac ccttgtcttt aggtgccaga actgtttgtc atgggaccaa     480
gacggtgtca ccggcggcat ttctaccagc aataagggg cccagctcgg ttgggtccag     540
gcgttcccct ctcccggcaa cccgactgc cctacccaga tcactctcag tcagcatgac     600
aacggtatgg ccagtgggg agctgccttt gacagcaaca ttgccaatcc ctcttatact     660
gcatgggctg ccaaggccac caagaccgtt accggtactt gcagtggtcc agtcacgacc     720
agtattgccg ccactcctgt tcccactggc gtttctttg actacattgt cgttggtggt     780
ggtgccggtg gtattcccgt cgctgacaag ctcagcgagt ccggtaagag cgtgctgctc     840
atcgagaagg gtttcgcttc cactggtgag catggtggta ctctgaagcc cgagtggctg     900
aataatacat cccttactcg cttcgatgtt cccggtcttt gcaaccagat ctggaaagac     960
tcggatggca ttgcctgctc cgataccgat cagatggccg ctgcgtgct cggcggtggt    1020
accgccatca cgccggtct ctggtacaag ccctacacca aggactggga ctacctcttc    1080
ccctctggct ggaagggcag cgatatcgcc ggtgctacca gcagagccct ctcccgcatt    1140
ccgggtacca ccactccttc tcaggatgga aagcgctacc ttcagcaggg tttcgaggtt    1200
cttgccaacg gctcaaggc gagcggctgg aaggaggtcg attccctcaa ggacagcgag    1260
cagaagaacc gcactttctc ccacacctca tacatgtaca tcaatggcga gcgtggcggt    1320
cctctagcga cttacctcgt cagcgccaag aagcgcagca acttcaagct gtggctcaac    1380
accgctgtca agcgcgtcat ccgtgagggc ggccacatta ccggtgtgga ggttgaggcc    1440
ttccgcaacg gcggctactc cggaatcatc cccgtcacca acaccaccgg ccgcgtcgtt    1500
ctttccgccg gcaccttcgg cagcgccaag atccttctcc gttccggcat tggcccaagg    1560
gaccagctcg aggtggtcaa ggcctccgcc gacggcccta ccatggtcag caactcgtcc    1620
```

```
tggattgacc tccccgtcgg ccacaacctg gttgaccaca ccaacaccga caccgtcatc    1680
cagcacaaca acgtgacctt ctacgacttt tacaaggctt gggacaaccc caacacgacc    1740
gacatgaacc tgtacctcaa tgggcgctcc ggcatcttcg cccaggccgc gcccaacatt    1800
ggccccttgt tctgggagga gatcacgggc gccgacggca tcgtccgtca gctgcactgg    1860
accgcccgcg tcgagggcag cttcgagacc cccgacggct acgccatgac catgagccag    1920
taccttggcc gtggcgccac ctcgcgcggc cgcatgaccc tcagccctac cctcaacacc    1980
gtcgtgtctg acctcccgta cctcaaggac cccaacgaca aggccgctgt cgttcagggt    2040
atcgtcaacc tccagaaggc tctcgccaac gtcaagggtc tcacctgggc ttaccctagc    2100
gccaaccaga cggctgctga ttttgttgac aagcaacccg taacctacca atcccgccgc    2160
tccaaccact ggatgggcac caacaagatg ggcaccgacg acggccgcag cggcggcacc    2220
gcagtcgtcg acaccaacac gcgcgtctat ggcaccgaca acctgtacgt ggtggacgcc    2280
tcgattttcc ccggtgtgcc gaccaccaac cctaccgcct acattgtcgt cgccgctgag    2340
catgccgcgg ccaaaatcct ggcgcaaccc gccaacgagg ccgttcccaa gtggggctgg    2400
tgcggcgggc cgacgtatac tggcagccag acgtgccagg cgccatataa gtgcgagaag    2460
cagaatgatt ggtattggca gtgtgtgtag                                    2490
```

<210> SEQ ID NO 13
<211> LENGTH: 2487
<212> TYPE: DNA
<213> ORGANISM: Artificial Sequence
<220> FEATURE:
<223> OTHER INFORMATION: codon optimized variant of M.thermophilum wild-
      type sequence of SEQ ID NO:2

<400> SEQUENCE: 13

```
atgagaactt cttctagact tatcggtgcc ttggccgcag ctttgcttcc ttctgccctt      60
gctcagaata acgttccaaa caccttact gaccctgact ccgtatcac tttcaacact      120 tggggacttg acgaggattc tccacagact cagggtggat tcactttcgg tgttgctttg     180
ccatccgacg ctttgactac tgacgcatct gagttcatcg gttacttgaa gtgtgctaga     240
aatgacgagt ccgatggtg tggtatttcc cttggtggtc ctatgactaa ctccttgttg     300
attactgctt ggcctcacga ggacactgtt tacacttcct tgagatttgc taccggatac     360
gccatgcctg acgtttacga gggtgatgct gaaatcaccc aagtctcttc ctctgtcaat     420
tccactcatt tctctttgat ctttagatgt aagaactgtt tgcaatggtc ccacggaggt     480
tcctctggtg gtgcttctac ctccggtggt gttcttgttc ttggttgggt ccaagctttt     540
gacgatccag gtaacccaac ctgtccagaa cagattactt gcagcaaca cgacaatgga     600 atgggtattt ggggtgcaca attgaatacc gatgctgcat ctccatccta taccgactgg     660
gctgcacaag ctaccaagac cgttaccggt gattgtgagg tcctactga cttctgtg      720 gtcggtgttc agttccaac tggagttct ttcgattaca ttgttgtcgg aggtggtgcc     780
ggaggtatcc cagcagctga caagctttct gaggctggta agtccgtttt gcttatgag     840 aagggtttcg cttctaccgc taataccgga ggtactttgg gtccagagtg gttggagggt     900
cacgatctta ctcgtttcga cgttccaggt ctttgcaacc aaatttgggt ggactctaag     960
ggaatcgctt gcgaggatac tgaccaaatg gcaggatgtg tcttggtgg aggtaccgca    1020 gtcaatgctg tctcttggtt caagccatat tcttggatt gggattactt gtttcctgac    1080
ggttggaagt acaacgacgt ccaacctgcc atcaacagag ctttgtctcg tattcctggt    1140
```

```
actgacgctc cttctactga cggaaagaga tactaccagg aaggttttga ggttctttct    1200
aaaggtttgg ccgctggtgg atggacctct gtgactgcaa acaatgctcc agacaagaag    1260
aaccgtacct tcgctcacgc acctttcatg ttcgcaggtg gagagagaaa cggtccattg    1320
ggtacctact ttcaaactgc caaaaagcgt aacaacttcg acgtctggct taacacttct    1380
gttaagagag ttatcagaga aggaggtcac attactggag ttgaagtgga gcctttcaga    1440
gatggaggtt acgagggtat cgtgcctgtg actaaggtta ctggacgtgt tatcttgtct    1500
gctggtactt tcggttccgc caagattctt ttgcgttccg gtattggacc agaggaccaa    1560
ttggaggtcg ttgccgcttc tgagaaggat ggacctacca tgatcggtaa ctcctcttgg    1620
attaacttgc ctgtgggata caacttggac gatcacttga acaccgacac cgtgatctct    1680
caccctgatg tggtcttcta tgacttttac gaggcttggg atgacccaat tgaatctgac    1740
aagaactctt acttggaatc tagaaccgga atcttggctc aagcagctcc aaacattggt    1800
ccaatgttct gggaagagat tgtgggagct gacggtattg tcagacaatt gcagtggacc    1860
gccagagttg agggttcttt gggtgcacct aacggacata ccatgaccat gtctcaatac    1920
cttggtcgtg gtgccacttc tagaggtaga atgaccatca ctccatcttt gaccactatt    1980
gtttccgacg tcccttacct taaagaccca aacgacaaag aagccgtgat tcaaggtatt    2040
atcaacttgc agaatgcttt gcagaacgtt gccaatttga cctggttgtt cccaaactct    2100
accattaccc cacgtgagta tgtcgaatct atggtcgtgt ctccttctaa cagacgttct    2160
aaccactgga tgggtactaa caaattgggt actgatgacg gtagaaaagg tggatccgca    2220
gtggttgact tggacactcg tgtctatggt accgataact tgttcgttat cgatgcttcc    2280
atcttccctg gtgttcctac cactaaccca acttcttaca ttgtcgttgc cgcagagcac    2340
gcttcctctc gtattcttgc attgccagac cttgagccag tccctaaata cggacagtgt    2400
ggtggaagag agtggactgg atctttcgtt tgcgcagatg gttctacctg tgaataccaa    2460
aatgagtggt actctcaatg tttgtaa                                        2487
```